United States Patent
Bamdad et al.

(10) Patent No.: US 11,898,160 B2
(45) Date of Patent: *Feb. 13, 2024

(54) METHOD FOR MAINTAINING PLURIPOTENCY IN CELLS

(75) Inventors: Cynthia C. Bamdad, Waltham, MA (US); Shawn P. Fessler, Arlington, MA (US)

(73) Assignee: MINERVA BIOTECHNOLOGIES CORPORATION, Waltham, MA (US)

(*) Notice: Subject to any disclaimer, the term of this patent is extended or adjusted under 35 U.S.C. 154(b) by 135 days.

This patent is subject to a terminal disclaimer.

(21) Appl. No.: 12/577,103

(22) Filed: Oct. 9, 2009

(65) Prior Publication Data

US 2010/0093092 A1 Apr. 15, 2010

Related U.S. Application Data

(60) Provisional application No. 61/104,231, filed on Oct. 9, 2008.

(51) Int. Cl.
*C12N 5/0735* (2010.01)
*C12N 5/074* (2010.01)

(52) U.S. Cl.
CPC ......... *C12N 5/0606* (2013.01); *C12N 5/0696* (2013.01); *C12N 2501/40* (2013.01); *C12N 2501/50* (2013.01); *C12N 2501/602* (2013.01); *C12N 2501/603* (2013.01); *C12N 2501/604* (2013.01); *C12N 2501/998* (2013.01)

(58) Field of Classification Search
CPC ........................ C12N 5/0606; C12N 5/0696; C12N 2501/40; C12N 2501/602; C12N 2501/603; C12N 2501/604; C12N 9/1229; C12Y 207/04006; G01N 33/5008–5041; G01N 33/5073
See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,675,189 A | 6/1987 | Kent et al. |
| 4,816,567 A | 3/1989 | Cabilly et al. |
| 5,075,109 A | 12/1991 | Tice et al. |
| 5,133,974 A | 7/1992 | Paradissis et al. |
| 5,225,539 A | 7/1993 | Winter |
| 5,407,686 A | 4/1995 | Patel et al. |
| 5,585,089 A | 12/1996 | Queen et al. |
| 5,693,762 A | 12/1997 | Queen et al. |
| 5,736,152 A | 4/1998 | Dunn |
| 5,834,217 A | 11/1998 | Levine et al. |
| 5,859,205 A | 1/1999 | Adair et al. |
| 7,129,058 B2 | 10/2006 | Yamashita |
| 7,700,715 B2 | 4/2010 | Bamdad et al. |
| 8,535,944 B2 | 9/2013 | Bamdad |
| 8,859,495 B2* | 10/2014 | Bamdad .................. A61P 35/00 514/7.6 |
| 10,703,821 B2 | 7/2020 | Bamdad |
| 2002/0156112 A1 | 10/2002 | Bamdad et al. |
| 2003/0036199 A1 | 2/2003 | Bamdad et al. |
| 2004/0009147 A1 | 1/2004 | Ebner et al. |
| 2006/0222637 A1* | 10/2006 | Bamdad ..................... 424/94.63 |
| 2020/0385485 A1 | 12/2020 | Bamdad |

FOREIGN PATENT DOCUMENTS

| | | | |
|---|---|---|---|
| EP | 0239400 A2 | 9/1987 | |
| WO | WO-8809344 A1 | 12/1988 | |
| WO | WO-8909622 A1 | 10/1989 | |
| WO | WO-9007861 A1 | 7/1990 | |
| WO | WO-9110741 A1 | 7/1991 | |
| WO | WO-9402602 A1 | 2/1994 | |
| WO | WO-9524929 A2 | 9/1995 | |
| WO | WO-9633735 A1 | 10/1996 | |
| WO | WO-9634096 A1 | 10/1996 | |
| WO | WO-0034783 A1 | 6/2000 | |
| WO | WO-0043791 A2 | 7/2000 | |
| WO | WO-02056022 A2 | 7/2002 | |
| WO | WO-03074074 A1 | 9/2003 | |
| WO | WO-03106495 A2 | 12/2003 | |
| WO | WO-2004002259 A2 | 1/2004 | |
| WO | WO-2004022590 A2 | 3/2004 | |
| WO | WO-2005019269 A2 * | 3/2005 | ............. B82Y 30/00 |
| WO | WO-2005056780 A2 * | 6/2005 | ........... C12N 5/0647 |
| WO | WO-2006105448 A2 | 10/2006 | |
| WO | WO-2007053135 A1 | 5/2007 | |
| WO | WO-2008070171 A2 | 6/2008 | |
| WO | WO-2010042562 A2 | 4/2010 | |
| WO | WO-2010042891 A2 | 4/2010 | |
| WO | WO-2010144887 A1 | 12/2010 | |

OTHER PUBLICATIONS

Willems et al (Experimental Hematology, 2002. vol. 30, pp. 640-648).*
Masip et al., Molecular Human Reproduction, vol. 16, No. 11, pp. 856-868, 2010.*
Entry for "Pluripotent cell" from Append B: Glossary in 2008 Amendments to the National Academies' Guidelines for Human Embryonic Stem Cell Research. Natl. Res. Counc. and Inst. of Med. Human Embryonic Stem Cell Research Advisor Committee. Washington (DC): National Academies Press, 2008, 1 page. (Year: 2008).*
Yamashita et al. Forskolin and phorbol ester have opposite effects on the expression of mucin-associated sialyl-Lewisâ in pancreatic cancer cells. European Journal of Cancer, vol. 36, No. 1, pp. 113-120, 2000. (Year: 2000).*

(Continued)

*Primary Examiner* — Jennifer Dunston

(74) *Attorney, Agent, or Firm* — WILSON SONSINI GOODRICH & ROSATI

(57) ABSTRACT

The present application describes a method for inducing or maintaining pluripotency in a cell by contacting the cell with a biological or chemical species that increases MUC1* activity.

18 Claims, 11 Drawing Sheets

Specification includes a Sequence Listing.

(56) References Cited

OTHER PUBLICATIONS

Snoek et al. Protein Kinase C and Phorbol Ester Receptor expression Related to Growth and Differentiation of Nullipotent and Pluripotent Embryonal Carcinoma Cells. Developmental Biology, vol. 115, No. 2, pp. 282-292, Jun. 1986. (Year: 1986).*
Andrews et al. Comparative analysis of cell surface antigens expressed by cell lines derived from human germ cell tumors. International Journal of Cancer, vol. 66, pp. 806-816, 1996. (Year: 1996).*
Maherali et al. A high-efficiency system for the generation and study of human induced pluripotent stem cells. Cell Stem Cell, vol. 3, No. 3, pp. 340-345, and pp. 1/7-7/4 of Supplemental Information, Sep. 11, 2008. (Year: 2008).*
Campbell et al. Oct4 targets regulatory nodes to modulate stem cell function. PLoS ONE, vol. 6, e553, Jun. 20, 2007, printed as pp. 1-11. (Year: 2007).*
Bilitou et al. The NM23 family in development. Molecular and Cellular Biochemistry, vol. 329, No. 1-2, pp. 17-33, May 7, 2009. (Year: 2009).*
Aoi, T. et al. Science 321, 699-702 (2008).
Boyer L. A. et al. Cell 122, 947-956 (2005).
Dexheimer at al. Mol Cancer Ther 8(5):1363-1377 (2009).
Fessler S. et al. Breast Cancer Res Treat. 118: 113-134 (2009).
Foster, K. W. et al. Oncogene 24(9):1491-1500 (2005).
Hikita et al. PLoS ONE 3(10), e3312 (2008).
Huang, L. et al. Cancer Res , 65(22):10413-22 (2005).
Huangfu D. et al. Nat Biotechnol 26(7), 795-797 (2008).
Huangfu D et al. Nat Biotechnol 26(11), 1269-1275 (2008).
Jaenisch, R. and Young, R. Cell 132, 567-582 (2008).
Kaji, K., et al. Nature 458(7239):771-775 (2009).
Kawamura et al., Nature 460:1140-4 (2009).
Kim, et al. Biochem Biophys Res Commun 307:281-289 (2003).
Komarov, et al. Science 285:1733-7 (1999).
Lin, T et al. Nat Cell Biol 7(2): 165-171 (2005).
Lowry, W.E. et al. Proc. Natl. Acad. Sci. USA 105(8):2883-2888 (2008).
Lyssiotis et al. Proc Natl Acad Sci USA 106(22):8912-8917 (2009).
Mahanta et al. PLoS ONE 3(4):e2054 (2008).
Maherali, N. et al. Cell Stem Cell 1:55-70 (2007).
Maimets, T et al., Oncogene 27:5277-5287 (2008).
Nakagawa, M. et al. Nature Biotechnol 26(1):101-106 (2008).
Okita, K et al. Nature 448:313-317 (2007).
Okita K et al. Science 322:949-953 (2008).
Park, I.H. et al. Nature 451:141-146 (2008).
Raina et al. Cancer Res 69(12):5133-5141 (2009).
Soldner F., et al. Cell 136:964-977 (2009).
Sommer C., et al., Stem Cells, 27:543-9 (2009).
Stadtfeld M., et al. Science 322, 945-949 (2008).
Strom, et al. Nat Chem Biol. 2(9):474-9 (2006).
Takahashi, K. & Yamanaka, S. Cell 126, 663-676 (2006).
Takahashi, K. et al. Cell 131:861-872 (2007).
Thathiah, A et al. J Biol Chem 278(5):3386-3394 (2003).
Vassilev, L. T. et al., Science 303, 844-848. (2004).
Wei et al. Cancer Res 67(4):1853-1858 (2007).
Wernig, M. et al. Nature 448, 318-324 (2007).
Wernig, M. et al. Cell Stem Cell 2, 10-12 (2008).
Woltjen, K., et al Nature 458, 766-770 (2009).
Yamanaka, S. Cell stem Cell 1, 39-49 (2007).
Yu, J. et al. Science 324, 797-801 (2009).
Yu, J. et al. Science 318, 1917-1920 (2007).
Zou et al. MCB, 20(2):628-633 (2000).
Zhou et al. Cell Stem Cell 4:381-384 (2009).
Al-Hajj et al. Prospective identification of tumorigenic breast cancer cells. PNAS 100(7):3983-3988 (2003).
Al-Hajj et al. Self-renewal and solid tumor stem cells. Oncogene, 23:7274-7282 (2004).
Allsopp et al. Comparison of numerous delivery systems for the induction of cytotoxic T lymphocytes by immunization. Eur. J. Immunol 26:1951-1959 (1996).
Altschul, et al. Gapped BLAST and PSI-BLAST: a new generation of protein database search programs. Nucleic Acids Res 25:3389-3402 (1997).
Bonnet et al. Human acute myeloid leukemia is organized as a hierarchy that originates from a primitive hematopoietic cell. Nat. Med. 3:730-737 (1997).
Briasoulis et al. G-CSF induces elevation of circulating CA 15-3 in breast carcinoma patients treated in an adjuvant setting. Cancer 91:909-917 (2001).
Burchell et al. Development and characterization of breast cancer reactive monoclonal antibodies directed to the core protein of the human milk mucin. Cancer Res., 47:5476-5482 (1987).
Byrd et al. Mucins and mucin binding proteins in colorectal cancer. Cancer Metastasis Review 23(1-2):77-99 (2004).
Chengalvala et al. Replication and immunogenicity of Ad7-, Ad4-, and Ad5-hepatitis B virus surface antigen recombinants, with or without a portion of E3 region, in chimpanzees. Vaccine 15:335-339 (1997).
Cloosen et al. Mucin-1 is expressed on dendritic cells, both in vitro and in vivo. Int. Immunol. 11:1561-71 (2004).
Dahiyat et al.: De novo protein design: fully automated sequence selection. Science 278(5335):82-87 (1997).
Davis et al. A viral vaccine vector that expresses foreign genes in lymph nodes and protects against mucosal challenge. J. Virol. 70:3781-3787 (1996).
Eloit et al. High level of transgene expression in cell cultures and in the mouse by replication-incompetent adenoviruses harboring modified VAI genes. J. Virol. 7:5375-5381 (1997).
Fraley et al. New generation liposomes: the engineering of an efficient vehicle for intracellular delivery of nucleic acids. Trends Biochem. Sci. 6:77 (1981).
Gendler, et al. Molecular cloning and expression of human tumor-associated polymorphic epithelial mucin. J Biol Chem. 265:15286-15293 (1990).
Goldspiel et al. Human gene therapy. Clin Pharm 12:488-505 (1993).
Gregoriadis. Liposomes for drugs and vaccines. Trends in Biotechnology 3:235-241 (1985).
Irwin et al. Direct injection of a recombinant retroviral vector induces human immunodeficiency virus-specific immune responses in mice and nonhuman primates. J. Virol. 68:5036-5044 (1994).
Jarrad et al. MUC1 is a novel marker for the type II pneumocyte lineage during lung carcinogenesis. Cancer Research, 58(23):5582-5589 (1998).
Koller et al. Inactivating the beta 2-microglobulin locus in mouse embryonic stem cells by homologous recombulion. PNAS USA 86:8932-8935 (1989).
Kufe, et al. Differential reactivity of a novel monoclonal antibody (DF3) with human malignant versus benign breast tumors. Hybridoma 3:223-232 (1984).
Lapidot, et al. (1994). A cell initiating human acute myeloid leukaemia after transplantation into SCID mice. Nature 367, 645-648.
Lascu et al. Quaternary Structure of Nucleoside Diphosphate Kineses. J Bioenerg Biomembr 32(3):227-236 (2000).
Leong et al. Epithelial membrane antigen (EMA) or MUC1 expression in monocytes and monoblasts. Pathology 35:422-427 (2003).
Ligtnberg et al. Episialin, a carcinoma associated mucin, is generated by a polymorphic gene encoding splice variants with alternative amino termini. J. Biol. Chem. 265:5573-5578 (1990).
MacDonald et al. Site-Directed Mutagenesis of nm23-HI. J Biol Chem 271(41):25107-25116 (1996).
Masip et al. Reprogramming with defined factors: from induced pluripotency to induced transdifferentiation. Molecular Human Reproduction 16(11):856-868 (2010).
Matsui et al. Characterization of clonogenic multiple myeloma cells. Blood 103:2332-2336 (2004).
Meseguer et al. Human endometrial mucin MUC1 is up-regulated by progesterone and down-regulated in vitro by the human blastocyst. Biol. Reprod. 64(2) 590-601 (2001).
Morgan et al. Human gene therapy. Ann Rev Biochem 62:191-217 (1993).

(56) References Cited

OTHER PUBLICATIONS

Moss. Genetically engineered poxviruses for recombinant gene expression, vaccination, and safety. PNAS USA 93:11341-11348 (1996).
Moss. Replicating and host-restricted non-replicating vaccinia virus vectors for vaccine development. Dev. Biol. Stand. 82:55-63 (1994).
Mulligan. The basic science of gene therapy. Science 260(5110):926-932 (1993).
Okabe-Kado et al., A New Function of Nrn231NDP Kinase as a Differentiation Inhibitory Factor, Which Does Not Require it's Kinase Activity. FEES Letters 363:311-315 (1995).
Okabe-Kado et al., Characterization of a Differentiation-Inhibitory Activity from Nondifferentiating Mouse Myeloid Leukemia cells. Cancer Research. 45:4848-4852 (1985).
Okabe-Kado et al. Identity of a differentiation inhibiting factor for mouse myeloid leukemia cells with NM23/nucleoside diphosphate kinase. Biochem Biophys Res Commun 182(3):987-994 (1992).
Okabe-Kado et al., Inhibitory Action of nm23 Proteins on Induction of Erythroid Differentiation of Human Leukemia Cells. Biochimica Biophys Acta 1267:101-106 (1995).
Okabe-Kado et al. Physiological and Pathological Relevance of Extracellular NM23INDP Kinases, J Bioenerg Biomembr 35(1):89-93 (2003).
Paoletti. Applications of pox virus vectors to vaccination: an update. PNAS USA 93:11349-11353 (1996).
PCT/US2009/060272 International Search Report and Written Opinion dated Oct. 17, 2012.
Pugachev et al. Double-subgenomic Sindbis virus recombinants expressing immunogenic proteins of Japanese encephalitis virus induce significant protection in mice against lethal JEV infection. Virology 212:587-594 (1995).
Rughetti et al. Regulated expression of MUC1 epithelial antigen in erythropoiesis. Br. J. Haematol 120(2):344-352 (2003).
Sawhney, et al. Bioerodible hydrogels based on photopolymerized poly(ethylene glycol)-co-poly(.alpha.-hydroxy acid) diacrylate macromers. Macromolecules 26(4):581-587 (1993).
Singh et al. Identification of a cancer stem cell in human brain tumors. Cancer Res., 63(18):5821-8 (2003).
Spicer et al. Molecular cloning and analysis of the mouse homologue of the tumor-associated mucin, MUC1, reveals conservation of potential O-glycosylation sites, transmembrane, and cytoplasmic domains and a loss of minisatellite-like polymorphism. J. Biol. Chem 266(23):15099-15109 (1991).
Stingl et al. Epithelial Progenitors in the Normal Human mammary Gland. Journal of Mammary Gland Biology and Neoplasia 10(1):49-59 (2005).
Tolstoshev. Gene Therapy, Concepts, Current Trials and Future Directions. Ann. Rev. Pharmacol. Toxicol. 32:573-596 (1993).
Townsend et al. Characterization of CD8+ cytotoxic T-lymphocyte responses after genetic immunization with retrovirus vectors expressing different forms of the hepatitis B virus core and e antigens. J. Virol. 71:3365-3374 (1997).
Vacanti et al. Identification and initial characterization of spore-like cells in adult mammals. J Cell Biochem 80:455-60 (2001).
Wu et al. Receptor-mediated in vitro gene transformation by a soluble DNA carrier system. J Biol Chem 262(10):4429-4432 (1987).
Wu et al. Delivery systems for gene therapy. Biotherapy 3:87-95 (1991).
Xiang et al. A replication-defective human adenovirus recombinant serves as a highly efficacious vaccine carrier. Virology 219:220-227 (1996).
Zhong et al. Evaluation of MUC1 and EGP40 in Bone marrow and Peripheral Blood as a Marker for Occult breast cancer. Arch Gynecol Obstet 264:177-181 (2001).
Zotter et al. Monoclonal antibodies to epithelial sialomucins recognize epitopes at different cellular sites in adenolymphomas of the parotid gland. Int J Cancer Suppl 3:38-44 (1988).

Adamo et al., AICAR activates the pluripotency transcriptional network in embryonic stem cells and induces KLF4 and KLF2 expression in fibroblasts BMC Pharmacology 9:2 (2009).
Alberts et al. Cell Biology: The Endless Frontier. Mol Biol Cell 21:129-130 (1994), printed as pp. 1/3-3/3.
Barratt-Boyes et al. Immunization of chimpanzees with tumor antigen MUC1 mucin tandem repeat peptide elicits both helper and cytotoxic T-cell responses. Clinical Cancer Research 5:1918-1924 (1999).
Burdon et al. Suppression of SHP-2 and ERK signalling promotes self-renewal of mouse embryonic stem cells. Dev Biol 210(1):30-43 (1999).
Clarke. Isolation and Characterization of Human Mammary Stem Cells. Cell Prolif. 38:375-386 (2005).
Corsten et al. Therapeutic stem-cells for cancer treatment: hopes and hurdles in tactical warfare. Cytotechncology 9:376-84 (2008).
Dubreuil-Lemaire et al. Lenograstim for the treatment of neutropenia in patients receiving ganciclovir for cytomegalovirus infection: a randomised, placebo-controlled trial in AIDS patients. Eur J Haematol 65:337-343 (2000).
Eridani et al. Siem cells: From embryology to cellular therapy? An appraisal of the present state of art. Cytotechnology 44:125-41 (2004).
Gad et al. Muc1-Derived Glycopeptide Libraries With Improved Mhc Anchors Are Strong Antigens and Prime Mouse T Cells for Proliferative Responses to Lysates of Human Breast Cancer Tissue. Eur. J Immunol 33:1624-1632 (2003).
Gervasi et al. nm23 influences proliferation and differentiation of PC12 cells in response to nerve growth factor. Cell Growth Differ 7:1689-1695 (1996).
Gollub et al. Regulation of mucin gene expression in secretory epithelial cells. Biochemical and Biophysical Research Communications 197(2):667-73 (1993) (Abstract).
Graham et al. Intramuscular immunisation with MUC1 cDNA can protect C57 mice challenged with MUC1-expressing syngeneic mouse tumour cells. Int J Cancer 65(5):664-70 (1996).
Guo et al. Klf4 reverts developmentally programmed restriction of ground state pluripotency. Development 136(7):1063-1069 (2009).
Han et al. Tumor initialing cancer stem cells from human breast cancer cell lines. Int J Oncol 34:1449-53 (2009).
Hanisch. Design of a Muc1-Based Cancer Vaccine. Biochem Soc Trans 33:705-708 (2005).
Joosten et al. Translational control of putative protooncogene Nm23-M2 by cytokines via phosphoinositide 3-kinase signaling. J Biol Chem 279(37):38169-76 (2004).
Kamata et al. Vaccination of mice with MUC1 cDNA suppresses the development of lung metastases. Clin Exp Metastasis 19(8):689-96 (2002).
Kunath et al. FGF stimulation of the Erk1/2 signalling cascade triggers transition of pluripotent embryonic stem cells from self-renewal to lineage commitment. Development 134(16):2895-902 (2007).
Kunkel. Rapid and efficient site-specific mutagenesis without phenotypic selection. PNAS USA 82:488-492 (1985).
Lakso et al. Embryonic Expression of nm23 during Mouse Organonesis. Cell Growth Differ 3:873-879 (1992).
Lin et al. Glial-derived nexin, a differentially expressed gene during neuronal differentiation, transforms HEK cells into neuron-like cells. Int J of Dev Neurosci 23:9-14 (2005).
Lombardi et al. nm23: Unraveling its Biological Function in Cell Differentiation. J Cell Physiol 182:144-149 (2000).
Luong et al. Expression of Nm23-H1 in AML correlates with white cell count at diagnosis and in vitro acts as a survival factor for primary AMLs cells: evidence of a novel autocrine survival factor in AML. Blood 102(part1of 2):2255 (2003).
Miyazaki et al. Overexpression of nm23-H2/NDP Kinase B in a Human Oral Squamous Cell Carcinoma Cell Line 36 Results in Reduced Metastasis, Differentiated Phenotype in the Metastatic Site, and Growth Factor-independent Proliferative Activity in Culture. Clin Cancer Res 5(12):4301-7 (1999).
Negroni et al. Neuroblastoma Specific Effects of DR-nrn23 and its Mutant Forms on Differentiation and Apoptosis. Cell Death Differ 7:843-850 (2000).

(56) References Cited

OTHER PUBLICATIONS

PCT/US2006/012092 International Search Report dated Nov. 13, 2006.
PCT/US2007/025047 International Search Report and Written Opinion dated Sep. 29, 2008.
Plunkett et al. Protection against MUC1 expressing mouse tumours by intra-muscular injection of MUC1 cDNA requires functional CO8+ and CD4+ T cells but does not require the MUC1 tandem repeat domain. Int J Cancer 109(5):691-7 (2004).
Sato et al. Maintenance of pluripotency in human and mouse embryonic stem cells through activation of Wnt signaling by a pharmacological GSK-3-specific inhibitor. Nat Med. 10(1):55-63 (2004).
Shan et al. Transplant for marrow stem cell on ischemic heart disease. Chinese Journal Clinical Pharmacology and Therapeutics 7(5):473-476 (2002), Abstract Only.
Shaw et al. Preferential transformation of human neuronal cells by human adenoviruses and the origin of HEK 293 cells. FASEB 16:869-71 (2002).
Silva et al. Capturing Pluripotency. Cell 132(4):532-6 (2008).
Silva et al., Promotion of reprogramming to ground state pluripotency by signal inhibition. PLOS Biol. 6(10):e253 (2008).
Sorscher et al. Microinjection of an NM23 specific antibody inhibits cell division in rat embryo fibroblasts. Biochem Biophy Res Commun 195(1):336-345 (1993).
Sridharan et al. Role of the murine reprogramming factors in the induction of pluripotency. Cell 136(2):364-377 (2009).
Stavridis et al. A discrete period of FGF-induced Erk1/2 signalling is required for vertebrate neural specification. Development 134:2889-2894 (2007).
Thathiah et al. MT1-MMP mediates MUC1 Shedding independent of TACE/ADAM17. Biochem. J. 382:363-373 (2004).
Thathiah et al., Tumor Necrosis Factor alpha Stimulates Muc1 Synthesis and Ectodomain Release in a Human Uterine Epithelial Cell Line. Endocrinology 145(9):4192-4203 (2004).
U.S. Appl. No. 11/278,122 Office Action dated Jan. 11, 2010.
U.S. Appl. No. 11/278,122 Office Action dated Jan. 31, 2008.
U.S. Appl. No. 11/278,122 Office Action dated May 3, 2010.
U.S. Appl. No. 11/278,122 Office Action dated Nov. 22, 2013.
U.S. Appl. No. 11/278,122 Office Action dated Oct. 31, 2008.
U.S. Appl. No. 11/278,122 Office Action dated Sep. 13, 2013.
U.S. Appl. No. 11/951,613 Office Action dated Jun. 19, 2015.
U.S. Appl. No. 11/951,613 Office Action dated Mar. 29, 2019.
U.S. Appl. No. 11/951,613 Office Action dated Mar. 7, 2014.
U.S. Appl. No. 11/951,613 Office Action dated Nov. 9, 2017.
U.S. Appl. No. 11/951,613 Office Action dated Oct. 18, 2010.
U.S. Appl. No. 11/951,613 Office Action dated Oct. 30, 2014.
U.S. Appl. No. 11/951,613 Office Action dated Sep. 14, 2016.
U.S. Appl. No. 14/480,586 Office Action dated Apr. 7, 2016.
U.S. Appl. No. 14/604,579 Office Action dated Sep. 13, 2022.
U.S. Appl. No. 16/921,352 Office Action dated May 5, 2021.
Venturelii et al. Overexpression of dr-nrn23, a protein encoded by a member of the nm23 gene family, inhibits granulocyte differentiation and induces apoptosis in 32d013 myeloid cells. PNAS USA 92:7435-7439 (1995).
Vertebrate—Wikipedia pp. 1-12; downloaded Sep. 6, 2022.
Wagner et al. Potent and selective inhibition of gene expression by an antisense heptanucleotide. Nat Biotechnol 14:840-844 (1996).
Wang et al., A shRNA functional screen reveals Nme6 and Nme7 are crucial for embryonic stem cell renewal. Stem Cells 30(10):2199-2211 (2012).
Waynesword.palomar.edu/trfeb98.htm pp. 1-19; downloaded Sep. 6, 2022.
Willems et al. Decrease in Nucleoside Diphosphate Kinase (NDPK/nm23) Expression during Hematopoietic Maturation. J Biol Chem 273(22):13663-8 (1998).
Wright et al. Cytotoxic T lymphocytes from humans with adenocarcinomas stimulated by native MUC1 mucin and a mucin peptide mutated at a glycosylation site. J Immunother 23(1)2-10 (2000).
Yunbin et al. Effect of hematopoietic growth factors on short expansion of umbilical cord blood CD34+ cells in vitro. Journal Fujian Medical College 37(2):147-50 (2003).
Zhao et al. Generation of cytotoxic and humoral immune responses by nonreplicative recombinant Semliki Forest virus. PNAS USA 92:3009-3013 (1995).
Zhou et al. Expression and purification of single chain anti-HBx antibody in E. coli. 123(11-12):609-13 (1997).
Zijlstra et al. Germ-line transmission of a disrupted β2-microglobulin gene produced by homologous recombination in embryonic stem cells. Nature 342:435-438 (1989).
Smagghe et al. MUC1* ligand, NM23-H1, is a novel growth factor that maintains human stem cells in a more naive state. PLOS One 8(3):E58601 (2013).

* cited by examiner

SEQUENCE LISTING

```
<160> NUMBER OF SEQ ID NOS: 34

<210> SEQ ID NO 1
<211> LENGTH: 1255
<212> TYPE: PRT
<213> ORGANISM: Homo sapiens
```

<400> SEQUENCE: 1

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415
```

```
Gly Val Thr Ser Ala Pro Asp Thr Arg Pro Ala Pro Gly Ser Thr Ala
                420                 425                 430
Pro Pro Ala His Gly Val Thr Ser Ala Pro Asp Thr Arg Pro Ala Pro
            435                 440                 445
Gly Ser Thr Ala Pro Pro Ala His Gly Val Thr Ser Ala Pro Asp Thr
        450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
                485                 490                 495
Gly Val Thr Ser Ala Pro Asp Thr Arg Pro Ala Pro Gly Ser Thr Ala
            500                 505                 510
Pro Pro Ala His Gly Val Thr Ser Ala Pro Asp Thr Arg Pro Ala Pro
            515                 520                 525
Gly Ser Thr Ala Pro Pro Ala His Gly Val Thr Ser Ala Pro Asp Thr
        530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
                565                 570                 575
Gly Val Thr Ser Ala Pro Asp Thr Arg Pro Ala Pro Gly Ser Thr Ala
            580                 585                 590
Pro Pro Ala His Gly Val Thr Ser Ala Pro Asp Thr Arg Pro Ala Pro
            595                 600                 605
Gly Ser Thr Ala Pro Pro Ala His Gly Val Thr Ser Ala Pro Asp Thr
        610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
                645                 650                 655
Gly Val Thr Ser Ala Pro Asp Thr Arg Pro Ala Pro Gly Ser Thr Ala
            660                 665                 670
Pro Pro Ala His Gly Val Thr Ser Ala Pro Asp Thr Arg Pro Ala Pro
            675                 680                 685
Gly Ser Thr Ala Pro Pro Ala His Gly Val Thr Ser Ala Pro Asp Thr
        690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
                725                 730                 735
Gly Val Thr Ser Ala Pro Asp Thr Arg Pro Ala Pro Gly Ser Thr Ala
            740                 745                 750
Pro Pro Ala His Gly Val Thr Ser Ala Pro Asp Thr Arg Pro Ala Pro
            755                 760                 765
Gly Ser Thr Ala Pro Pro Ala His Gly Val Thr Ser Ala Pro Asp Thr
        770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
                805                 810                 815
Gly Val Thr Ser Ala Pro Asp Thr Arg Pro Ala Pro Gly Ser Thr Ala
            820                 825                 830
```

```
Pro Pro Ala His Gly Val Thr Ser Ala Pro Asp Thr Arg Pro Ala Pro
            835                 840                 845

Gly Ser Thr Ala Pro Pro Ala His Gly Val Thr Ser Ala Pro Asp Thr
850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
            885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
            915                 920                 925

Gly Ser Thr Ala Pro Pro Ala His Gly Val Thr Ser Ala Pro Asp Asn
930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Ser Thr His Ser Ser Val Pro
            1010                1015                1020

Pro Leu Thr Ser Ser Asn His Ser Thr Ser Pro Gln Leu Ser Thr
            1025                1030                1035

Gly Val Ser Phe Phe Phe Leu Ser Phe His Ile Ser Asn Leu Gln
            1040                1045                1050

Phe Asn Ser Ser Leu Glu Asp Pro Ser Thr Asp Tyr Tyr Gln Glu
            1055                1060                1065

Leu Gln Arg Asp Ile Ser Glu Met Phe Leu Gln Ile Tyr Lys Gln
            1070                1075                1080

Gly Gly Phe Leu Gly Leu Ser Asn Ile Lys Phe Arg Pro Gly Ser
            1085                1090                1095

Val Val Val Gln Leu Thr Leu Ala Phe Arg Glu Gly Thr Ile Asn
            1100                1105                1110

Val His Asp Val Glu Thr Gln Phe Asn Gln Tyr Lys Thr Glu Ala
            1115                1120                1125

Ala Ser Arg Tyr Asn Leu Thr Ile Ser Asp Val Ser Val Ser Asp
            1130                1135                1140

Val Pro Phe Pro Phe Ser Ala Gln Ser Gly Ala Gly Val Pro Gly
            1145                1150                1155

Trp Gly Ile Ala Leu Leu Val Leu Val Cys Val Leu Val Ala Leu
            1160                1165                1170

Ala Ile Val Tyr Leu Ile Ala Leu Ala Val Cys Gln Cys Arg Arg
            1175                1180                1185

Lys Asn Tyr Gly Gln Leu Asp Ile Phe Pro Ala Arg Asp Thr Tyr
            1190                1195                1200

His Pro Met Ser Glu Tyr Pro Thr Tyr His Thr His Gly Arg Tyr
            1205                1210                1215

Val Pro Pro Ser Ser Thr Asp Arg Ser Pro Tyr Glu Lys Val Ser
            1220                1225                1230

Ala Gly Asn Gly Gly Ser Ser Leu Ser Tyr Thr Asn Pro Ala Val
```

```
                1235                1240                1245

Ala Ala  Ala Ser Ala Asn Leu
         1250                1255

<210> SEQ ID NO 2
<211> LENGTH: 19
<212> TYPE: PRT
<213> ORGANISM: Homo sapiens

<400> SEQUENCE: 2

Met Thr Pro Gly Thr Gln Ser Pro Phe Phe Leu Leu Leu Leu Thr
1               5                   10                  15

Val Leu Thr

<210> SEQ ID NO 3
<211> LENGTH: 23
<212> TYPE: PRT
<213> ORGANISM: Homo sapiens

<400> SEQUENCE: 3

Met Thr Pro Gly Thr Gln Ser Pro Phe Phe Leu Leu Leu Leu Thr
1               5                   10                  15

Val Leu Thr Val Val Thr Ala
            20

<210> SEQ ID NO 4
<211> LENGTH: 23
<212> TYPE: PRT
<213> ORGANISM: Homo sapiens

<400> SEQUENCE: 4

Met Thr Pro Gly Thr Gln Ser Pro Phe Phe Leu Leu Leu Leu Thr
1               5                   10                  15

Val Leu Thr Val Val Thr Gly
            20

<210> SEQ ID NO 5
<211> LENGTH: 146
<212> TYPE: PRT
<213> ORGANISM: Homo sapiens

<400> SEQUENCE: 5

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala Gly Val Pro
        35                  40                  45

Gly Trp Gly Ile Ala Leu Leu Val Leu Val Cys Val Leu Val Ala Leu
    50                  55                  60

Ala Ile Val Tyr Leu Ile Ala Leu Ala Val Cys Gln Cys Arg Arg Lys
65                  70                  75                  80

Asn Tyr Gly Gln Leu Asp Ile Phe Pro Ala Arg Asp Thr Tyr His Pro
                85                  90                  95

Met Ser Glu Tyr Pro Thr Tyr His Thr His Gly Arg Tyr Val Pro Pro
            100                 105                 110

Ser Ser Thr Asp Arg Ser Pro Tyr Glu Lys Val Ser Ala Gly Asn Gly
        115                 120                 125

Gly Ser Ser Leu Ser Tyr Thr Asn Pro Ala Val Ala Ala Ala Ser Ala
```

Asn Leu
145

<210> SEQ ID NO 6
<211> LENGTH: 45
<212> TYPE: PRT
<213> ORGANISM: Homo sapiens

<400> SEQUENCE: 6

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 7
<211> LENGTH: 44
<212> TYPE: PRT
<213> ORGANISM: Homo sapiens

<400> SEQUENCE: 7

Thr Ile Asn Val His Asp Val Glu Thr Gln Phe Asn Gln Tyr Lys Thr
1               5                   10                  15

Glu Ala Ala Ser Arg Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 8
<211> LENGTH: 45
<212> TYPE: PRT
<213> ORGANISM: Homo sapiens

<400> SEQUENCE: 8

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 9
<211> LENGTH: 44
<212> TYPE: PRT
<213> ORGANISM: Homo sapiens

<400> SEQUENCE: 9

Thr Ile Asn Val His Asp Val Glu Thr Gln Phe Asn Gln Tyr Lys Thr
1               5                   10                  15

Glu Ala Ala Ser Pro Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 10
<211> LENGTH: 216
<212> TYPE: DNA
<213> ORGANISM: Homo sapiens

```
<400> SEQUENCE: 10
tgtcagtgcc gccgaaagaa ctacgggcag ctggacatct ttccagcccg ggatacctac      60
catcctatga gcgagtaccc cacctaccac acccatgggc gctatgtgcc ccctagcagt     120
accgatcgta gccctatga gaaggtttct gcaggtaacg gtggcagcag cctctcttac     180
acaaacccag cagtggcagc cgcttctgcc aacttg                              216

<210> SEQ ID NO 11
<211> LENGTH: 72
<212> TYPE: PRT
<213> ORGANISM: Homo sapiens

<400> SEQUENCE: 11

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Ala Ser Ala Asn Leu
65                  70

<210> SEQ ID NO 12
<211> LENGTH: 854
<212> TYPE: DNA
<213> ORGANISM: Homo sapiens

<400> SEQUENCE: 12
gagatcctga gacaatgaat catagtgaaa gattcgtttt cattgcagag tggtatgatc      60
caaatgcttc acttcttcga cgttatgagc ttttatttta cccaggggat ggatctgttg     120
aaatgcatga tgtaaagaat catcgcacct ttttaaagcg gaccaaatat gataacctgc     180
acttggaaga tttatttata ggcaacaaag tgaatgtctt ttctcgacaa ctggtattaa     240
ttgactatgg ggatcaatat acagctcgcc agctgggcag taggaaagaa aaaacgctag     300
ccctaattaa accagatgca atatcaaagg ctggagaaat aattgaaata ataaacaaag     360
ctggatttac tataaccaaa ctcaaaatga tgatgctttc aaggaaagaa gcattggatt     420 tcatgtaga tcaccagtca agaccctttt tcaatgagct gatccagttt attacaactg     480
gtcctattat tgccatggag attttaagag atgatgctat atgtgaatgg aaaagactgc     540
tgggacctgc aaactctgga gtggcacgca cagatgcttc tgaaagcatt agagccctct     600
ttggaacaga tggcataaga aatgcagcgc atggccctga ttcttttgct tctgcggcca     660
gagaaatgga gttgttttt ccttcaagtg gaggttgtgg gccggcaaac actgctaaat     720
ttactaattg tacctgttgc attgttaaac cccatgctgt cagtgaaggt atgttgaata     780
cactatattc agtacatttt gttaatagga gagcaatgtt tattttcttg atgtacttta     840
tgtatagaaa ataa                                                      854

<210> SEQ ID NO 13
<211> LENGTH: 283
<212> TYPE: PRT
<213> ORGANISM: Homo sapiens

<400> SEQUENCE: 13
```

```
Asp Pro Glu Thr Met Asn His Ser Glu Arg Phe Val Phe Ile Ala Glu
1               5                   10                  15

Trp Tyr Asp Pro Asn Ala Ser Leu Leu Arg Arg Tyr Glu Leu Leu Phe
            20                  25                  30

Tyr Pro Gly Asp Gly Ser Val Glu Met His Asp Val Lys Asn His Arg
        35                  40                  45

Thr Phe Leu Lys Arg Thr Lys Tyr Asp Asn Leu His Leu Glu Asp Leu
    50                  55                  60

Phe Ile Gly Asn Lys Val Asn Val Phe Ser Arg Gln Leu Val Leu Ile
65                  70                  75                  80

Asp Tyr Gly Asp Gln Tyr Thr Ala Arg Gln Leu Gly Ser Arg Lys Glu
                85                  90                  95

Lys Thr Leu Ala Leu Ile Lys Pro Asp Ala Ile Ser Lys Ala Gly Glu
            100                 105                 110

Ile Ile Glu Ile Ile Asn Lys Ala Gly Phe Thr Ile Thr Lys Leu Lys
            115                 120                 125

Met Met Met Leu Ser Arg Lys Glu Ala Leu Asp Phe His Val Asp His
    130                 135                 140

Gln Ser Arg Pro Phe Phe Asn Glu Leu Ile Gln Phe Ile Thr Thr Gly
145                 150                 155                 160

Pro Ile Ile Ala Met Glu Ile Leu Arg Asp Asp Ala Ile Cys Glu Trp
                165                 170                 175

Lys Arg Leu Leu Gly Pro Ala Asn Ser Gly Val Ala Arg Thr Asp Ala
            180                 185                 190

Ser Glu Ser Ile Arg Ala Leu Phe Gly Thr Asp Gly Ile Arg Asn Ala
        195                 200                 205

Ala His Gly Pro Asp Ser Phe Ala Ser Ala Ala Arg Glu Met Glu Leu
    210                 215                 220

Phe Phe Pro Ser Ser Gly Gly Cys Gly Pro Ala Asn Thr Ala Lys Phe
225                 230                 235                 240

Thr Asn Cys Thr Cys Cys Ile Val Lys Pro His Ala Val Ser Glu Gly
                245                 250                 255

Met Leu Asn Thr Leu Tyr Ser Val His Phe Val Asn Arg Arg Ala Met
            260                 265                 270

Phe Ile Phe Leu Met Tyr Phe Met Tyr Arg Lys
        275                 280

<210> SEQ ID NO 14
<211> LENGTH: 534
<212> TYPE: DNA
<213> ORGANISM: Homo sapiens

<400> SEQUENCE: 14
atggtgctac tgtctacttt agggatcgtc tttcaaggcg aggggcctcc tatctcaagc      60
tgtgatacag gaaccatggc caactgtgag cgtaccttca ttgcgatcaa accagatggg     120
gtccagcggg tcttgtggga gagattatc aagcgttttg agcagaaagg attccgcctt     180
gttggtctga aattcatgca agcttccgaa gatcttctca ggaacactac gttgacctg      240 aaggaccgtc cattctttgc cggcctggtg aaatacatgc actcagggcc ggtagttgcc     300
atggtctggg aggggctgaa tgtggtgaag acgggccgag tcatgctcgg ggagaccaac     360
cctgcagact ccaagcctgg gaccatccgt ggagacttct gcatacaagt tggcaggaac     420
attatacatg gcagtgattc tgtggagagt gcagagaagg gatcggctt gtggtttcac      480 cctgaggaac tggtagatta cacgagctgt gctcagaact ggatctatga atga           534
```

<210> SEQ ID NO 15
<211> LENGTH: 177
<212> TYPE: PRT
<213> ORGANISM: Homo sapiens

<400> SEQUENCE: 15

Met Val Leu Leu Ser Thr Leu Gly Ile Val Phe Gln Gly Glu Gly Pro
1               5                   10                  15

Pro Ile Ser Ser Cys Asp Thr Gly Thr Met Ala Asn Cys Glu Arg Thr
            20                  25                  30

Phe Ile Ala Ile Lys Pro Asp Gly Val Gln Arg Gly Leu Val Gly Glu
        35                  40                  45

Ile Ile Lys Arg Phe Glu Gln Lys Gly Phe Arg Leu Val Gly Leu Lys
    50                  55                  60

Phe Met Gln Ala Ser Glu Asp Leu Leu Lys Glu His Tyr Val Asp Leu
65                  70                  75                  80

Lys Asp Arg Pro Phe Phe Ala Gly Leu Val Lys Tyr Met His Ser Gly
                85                  90                  95

Pro Val Val Ala Met Val Trp Glu Gly Leu Asn Val Val Lys Thr Gly
            100                 105                 110

Arg Val Met Leu Gly Glu Thr Asn Pro Ala Asp Ser Lys Pro Gly Thr
        115                 120                 125

Ile Arg Gly Asp Phe Cys Ile Gln Val Gly Arg Asn Ile Ile His Gly
    130                 135                 140

Ser Asp Ser Val Glu Ser Ala Glu Lys Glu Ile Gly Leu Trp Phe His
145                 150                 155                 160

Pro Glu Glu Leu Val Asp Tyr Thr Ser Cys Ala Gln Asn Trp Ile Tyr
                165                 170                 175

Glu

<210> SEQ ID NO 16
<211> LENGTH: 534
<212> TYPE: DNA
<213> ORGANISM: Homo sapiens

<400> SEQUENCE: 16
atggtgctac tgtctacttt agggatcgtc tttcaaggcg aggggcctcc tatctcaagc      60
tgtgatacag gaaccatggc caactgtgag cgtaccttca ttgcgatcaa accagatggg     120
gtccagcggg gtcttgtggg agagattatc aagcgttttg agcagaaagg attccgcctt     180
gttggtctga aattcatgca agcttccgaa gatcttctca ggaacactta cgttgacctg     240
aaggaccgtc cattctttgc cggcctggtg aaatacatgc actcagggcc ggtagttgcc     300
atggtctggg aggggctgaa tgtggtgaag acgggccgag tcatgctcgg ggagaccaac     360
cctgcagact ccaagcctgg gaccatccgt ggagacttct gcatacaagt tggcaggaac     420
attatacatg gcggtgattc tgtggagagt gcagagaagg agatcggctt gtggtttcac     480
cctgaggaac tggtagatta cacgagctgt gctcagaact ggatctatga atga           534

<210> SEQ ID NO 17
<211> LENGTH: 177
<212> TYPE: PRT
<213> ORGANISM: Homo sapiens

<400> SEQUENCE: 17

Met Val Leu Leu Ser Thr Leu Gly Ile Val Phe Gln Gly Glu Gly Pro

```
            1               5              10              15
          Pro Ile Ser Ser Cys Asp Thr Gly Thr Met Ala Asn Cys Glu Arg Thr
                           20                  25                  30

Phe Ile Ala Ile Lys Pro Asp Gly Val Gln Arg Gly Leu Val Gly Glu
                           35                  40                  45

Ile Ile Lys Arg Phe Glu Gln Lys Gly Phe Arg Leu Val Gly Leu Lys
                  50                  55                  60

Phe Met Gln Ala Ser Glu Asp Leu Leu Lys Glu His Tyr Val Asp Leu
          65                  70                  75                  80

Lys Asp Arg Pro Phe Phe Ala Gly Leu Val Lys Tyr Met His Ser Gly
                                85                  90                  95

Pro Val Val Ala Met Val Trp Glu Gly Leu Asn Val Val Lys Thr Gly
                          100                 105                 110

Arg Val Met Leu Gly Glu Thr Asn Pro Ala Asp Ser Lys Pro Gly Thr
                          115                 120                 125

Ile Arg Gly Asp Phe Cys Ile Gln Val Gly Arg Asn Ile Ile His Gly
                  130                 135                 140

Ser Asp Ser Val Glu Ser Ala Glu Lys Glu Ile Gly Leu Trp Phe His
          145                 150                 155                 160

Pro Glu Glu Leu Val Asp Tyr Thr Ser Cys Ala Gln Asn Trp Ile Tyr
                          165                 170                 175

Glu

<210> SEQ ID NO 18
<211> LENGTH: 954
<212> TYPE: DNA
<213> ORGANISM: Homo sapiens

<400> SEQUENCE: 18
atgtacaaca tgatggagac ggagctgaag ccgccgggcc cgcagcaaac ttcgggggc       60 ggcggcggca actccaccgc ggcggcggcc ggcggcaacc agaaaaacag cccgaccgc      120 gtcaagcggc ccatgaatgc cttcatggtg tggtcccgcg ggcagcggcg caagatggcc     180
caggagaacc ccaagatgca caactcggag atcagcaagc gcctgggcgc cgagtggaaa     240
cttttgtcgg agacggagaa gcggccgttc atcgacgagg ctaagcggct gcgagcgctg     300
cacatgaagg agcacccgga ttataaatac cggcccggc ggaaaaccaa gacgctcatg      360
aagaaggata gtacacgct gcccggcggg ctgctggccc ccggcggcaa tagcatggcg      420
agcggggtcg gggtgggcgc cggcctgggc gcgggcgtga accagcgcat ggacagttac     480
gcgcacatga acggctggag caacggcagc tacagcatga tgcaggacca gctgggctac     540
ccgcagcacc cgggcctcaa tgcgcacggc gcagcgcaga tgcagcccat gcaccgctac     600
gacgtgagcg ccctgcagta caactccatg accagctcgc agacctacat gaacggctcg     660
cccacctaca gcatgtccta ctcgcagcag ggcaccctg gcatggctct tggctccatg      720
ggttcggtgg tcaagtccga ggccagctcc agcccctg tggttacctc ttcctcccac       780
tccagggcgc cctgccaggc cggggacctc cgggacatga tcagcatgta tctccccggc     840
gccgaggtgc cggaacccgc cgcccccagc agacttcaca tgtcccagca ctaccagagc     900 ggccccggtgc ccggcacggc cattaacggg acactgcccc tctcacacat gtga          954

<210> SEQ ID NO 19
<211> LENGTH: 317
<212> TYPE: PRT
<213> ORGANISM: Homo sapiens
```

<400> SEQUENCE: 19

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315

<210> SEQ ID NO 20
<211> LENGTH: 1083
<212> TYPE: DNA
<213> ORGANISM: Homo sapiens

<400> SEQUENCE: 20
atggcgggac acctggcttc agattttgcc ttctcgcccc ctccaggtgg tggaggtgat       60
gggccagggg ggccggagcc gggctgggtt gatcctcgga cctggctaag cttccaaggc      120
cctcctggag ggccaggaat cgggccgggg gttgggccag gctctgaggt gtggggggatt     180 ccccccatgcc ccccgccgta tgagttctgt ggggggatgg cgtactgtgg gccccaggtt    240

```
ggagtggggc tagtgcccca aggcggcttg gagacctctc agcctgaggg cgaagcagga    300
gtcggggtgg agagcaactc cgatggggcc tccccggagc cctgcaccgt caccctggt    360 gccgtgaagc tggagaagga gaagctggag caaaacccgg aggagtccca ggacatcaaa    420
gctctgcaga aagaactcga gcaatttgcc aagctcctga agcagaagag gatcaccctg    480
ggatatacac aggccgatgt ggggctcacc ctgggggttc tatttgggaa ggtattcagc    540
caaacgacca tctgccgctt tgaggctctg cagcttagct tcaagaacat gtgtaagctg    600
cggcccttgc tgcagaagtg ggtggaggaa gctgacaaca atgaaaatct tcaggagata    660
tgcaaagcag aaaccctcgt gcaggcccga aagagaaagc gaaccagtat cgagaaccga    720
gtgagaggca acctggagaa tttgttcctg cagtgcccga aacccacact gcagcagatc    780
agccacatcg cccagcagct tgggctcgag aaggatgtgg tccgagtgtg gttctgtaac    840
cggcgccaga agggcaagcg atcaagcagc gactatgcac aacgagagga ttttgaggct    900
gctgggtctc ctttctcagg gggaccagtg tcctttcctc tggccccagg gccccatttt    960
ggtaccccag gctatgggag ccctcacttc actgcactgt actcctcggt ccctttccct   1020
gagggggaag cctttccccc tgtctctgtc accactctgg gctctcccat gcattcaaac   1080
tga                                                                 1083

<210> SEQ ID NO 21
<211> LENGTH: 360
<212> TYPE: PRT
<213> ORGANISM: Homo sapiens

<400> SEQUENCE: 21

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220
```

```
Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360
```

<210> SEQ ID NO 22
<211> LENGTH: 459
<212> TYPE: DNA
<213> ORGANISM: Homo sapiens

<400> SEQUENCE: 22

```
atggccaacc tggagcgcac cttcatcgcc atcaagccgg acggcgtgca gcgcggcctg    60
gtgggcgaga tcatcaagcg cttcgagcag aagggattcc gcctcgtggc catgaagttc   120
ctccgggcct ctgaagaaca cctgaagcag cactacattg acctgaaaga ccgaccattc   180
ttccctgggc tggtgaagta catgaactca gggccggttg tggccatggt ctgggagggg   240
ctgaacgtgg tgaagacagg ccgagtgatg cttggggaga ccaatccagc agattcaaag   300
ccaggcacca ttcgtgggga cttctgcatt caggttggca ggaacatcat tcatggcagt   360
gattcagtaa aaagtgctga aaagaaatc agcctatggt ttaagcctga gaactggtt    420 gactacaagt cttgtgctca tgactgggtc tatgaataa                          459
```

<210> SEQ ID NO 23
<211> LENGTH: 152
<212> TYPE: PRT
<213> ORGANISM: Homo sapiens

<400> SEQUENCE: 23

```
Met Ala Asn Leu Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Ala Met Lys Phe Leu Arg Ala Ser Glu Glu His Leu
        35                  40                  45

Lys Gln His Tyr Ile Asp Leu Lys Asp Arg Pro Phe Phe Pro Gly Leu
    50                  55                  60

Val Lys Tyr Met Asn Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
```

```
                100               105                110
Gly Arg Asn Ile Ile His Gly Ser Asp Ser Val Lys Ser Ala Glu Lys
            115                 120                 125

Glu Ile Ser Leu Trp Phe Lys Pro Glu Glu Leu Val Asp Tyr Lys Ser
    130                 135                 140

Cys Ala His Asp Trp Val Tyr Glu
145                 150
```

<210> SEQ ID NO 24
<211> LENGTH: 1410
<212> TYPE: DNA
<213> ORGANISM: Homo sapiens

<400> SEQUENCE: 24

```
atggctgtca gcgacgcgct gctcccatct ttctccacgt tcgcgtctgg cccggcggga      60
agggagaaga cactgcgtca agcaggtgcc ccgaataacc gctggcggga ggagctctcc     120
cacatgaagc gacttccccc agtgcttccc gccggcccct atgacctggc ggcggcgacc     180
gtggccacag acctggagag cgccggagcc ggtgcggctt gcggcggtag caacctggcg     240
cccctacctc ggagagagac cgaggagttc aacgatctcc tggacctgga ctttattctc     300
tccaattcgc tgacccatcc tccggagtca gtggccgcca ccgtgtcctc gtcagcgtca     360
gcctcctctt cgtcgtcgcc gtcgagcagc ggccctgcca gcgcgccctc acctgcagc     420
ttcacctatc cgatccgggc cgggaacgac ccgggcgtgg cgccgggcgg cacgggcgga     480
ggcctcctct atggcaggga gtccgctccc cctccgacgg ctcccttcaa cctggcggac     540
atcaacgacg tgagcccctc gggcggcttc gtggccgagc tcctgcggcc agaattggac     600
ccggtgtaca ttccgccgca gcagccgcag ccgccaggtg gcgggctgat gggcaagttc     660
gtgctgaagg cgtcgctgag cgcccctggc agcgagtacg gcagcccgtc ggtcatcagc     720
gtcacgaaag cagccctga cggcagccac ccggtggtgg tggcgcccta acggcggg     780
ccgccgcgca cgtgcccaa gatcaagcag gaggcggtct cttcgtgcac ccacttgggc     840
gctggacccc ctctcagcaa tggccaccgg ccggctgcac acgacttccc cctggggcgg     900
cagctcccca gcaggactac cccgaccctg ggtcttgagg aagtgctgag cagcagggac     960
tgtcaccctg ccctgccgct tcctcccggc ttccatcccc acccggggcc caattaccca    1020
tccttcctgc ccgatcagat gcagccgcaa gtcccgccgc tccattacca agagctcatg    1080
ccacccggtt cctgcatgcc agaggagccc aagccaaaga ggggaagacg atcgtggccc    1140
cggaaaagga ccgccaccca cacttgtgat tacgcgggct gcggcaaaac ctacacaaag    1200
agttcccatc tcaaggcaca cctgcgaacc cacacaggtg agaaaccta ccactgtgac    1260
tgggacggct gtgatggaa attcgcccgc tcagatgaac tgaccaggca ctaccgtaaa    1320
cacacggggc accgccgtt ccagtgccaa aaatgcgacc gagcattttc caggtcggac    1380
cacctcgcct acacatgaa gaggcatttt                                      1410
```

<210> SEQ ID NO 25
<211> LENGTH: 470
<212> TYPE: PRT
<213> ORGANISM: Homo sapiens

<400> SEQUENCE: 25

```
Met Ala Val Ser Asp Ala Leu Leu Pro Ser Phe Ser Thr Phe Ala Ser
1               5                   10                  15

Gly Pro Ala Gly Arg Glu Lys Thr Leu Arg Gln Ala Gly Ala Pro Asn
```

```
            20                  25                  30
Asn Arg Trp Arg Glu Glu Leu Ser His Met Lys Arg Leu Pro Pro Val
            35                  40                  45
Leu Pro Ala Gly Pro Tyr Asp Leu Ala Ala Thr Val Ala Thr Asp
 50                  55                  60
Leu Glu Ser Ala Gly Ala Ala Cys Gly Ser Asn Leu Ala
 65                  70                  75                  80
Pro Leu Pro Arg Arg Glu Thr Glu Glu Phe Asn Asp Leu Leu Asp Leu
                85                  90                  95
Asp Phe Ile Leu Ser Asn Ser Leu Thr His Pro Pro Glu Ser Val Ala
                100                 105                 110
Ala Thr Val Ser Ser Ser Ala Ser Ala Ser Ser Ser Ser Pro Ser
            115                 120                 125
Ser Ser Gly Pro Ala Ser Ala Pro Ser Thr Cys Ser Phe Thr Tyr Pro
            130                 135                 140
Ile Arg Ala Gly Asn Asp Pro Gly Val Ala Pro Gly Gly Thr Gly Gly
145                 150                 155                 160
Gly Leu Leu Tyr Gly Arg Glu Ser Ala Pro Pro Thr Ala Pro Phe
                165                 170                 175
Asn Leu Ala Asp Ile Asn Asp Val Ser Pro Ser Gly Gly Phe Val Ala
                180                 185                 190
Glu Leu Leu Arg Pro Glu Leu Asp Pro Val Tyr Ile Pro Pro Gln Gln
            195                 200                 205
Pro Gln Pro Pro Gly Gly Gly Leu Met Gly Lys Phe Val Leu Lys Ala
        210                 215                 220
Ser Leu Ser Ala Pro Gly Ser Glu Tyr Gly Ser Pro Ser Val Ile Ser
225                 230                 235                 240
Val Thr Lys Gly Ser Pro Asp Gly Ser His Pro Val Val Val Ala Pro
                245                 250                 255
Tyr Asn Gly Gly Pro Pro Arg Thr Cys Pro Lys Ile Lys Gln Glu Ala
                260                 265                 270
Val Ser Ser Cys Thr His Leu Gly Ala Gly Pro Pro Leu Ser Asn Gly
        275                 280                 285
His Arg Pro Ala Ala His Asp Phe Pro Leu Gly Arg Gln Leu Pro Ser
        290                 295                 300
Arg Thr Thr Pro Thr Leu Gly Leu Glu Glu Val Leu Ser Ser Arg Asp
305                 310                 315                 320
Cys His Pro Ala Leu Pro Leu Pro Pro Gly Phe His Pro His Pro Gly
                325                 330                 335
Pro Asn Tyr Pro Ser Phe Leu Pro Asp Gln Met Gln Pro Gln Val Pro
                340                 345                 350
Pro Leu His Tyr Gln Glu Leu Met Pro Pro Gly Ser Cys Met Pro Glu
                355                 360                 365
Glu Pro Lys Pro Lys Arg Gly Arg Arg Ser Trp Pro Arg Lys Arg Thr
                370                 375                 380
Ala Thr His Thr Cys Asp Tyr Ala Gly Cys Gly Lys Thr Tyr Thr Lys
385                 390                 395                 400
Ser Ser His Leu Lys Ala His Leu Arg Thr His Thr Gly Glu Lys Pro
                405                 410                 415
Tyr His Cys Asp Trp Asp Gly Cys Gly Trp Lys Phe Ala Arg Ser Asp
                420                 425                 430
Glu Leu Thr Arg His Tyr Arg Lys His Thr Gly His Arg Pro Phe Gln
                435                 440                 445
```

Cys Gln Lys Cys Asp Arg Ala Phe Ser Arg Ser Asp His Leu Ala Leu
    450                 455                 460

His Met Lys Arg His Phe
465                 470

<210> SEQ ID NO 26
<211> LENGTH: 1362
<212> TYPE: DNA
<213> ORGANISM: Homo sapiens

<400> SEQUENCE: 26

| | | | | | |
|---|---|---|---|---|---|
| atggattttt | ttcgggtagt | ggaaaaccag | cagcctcccg | cgacgatgcc | cctcaacgtt | 60 |
| agcttcacca | acaggaacta | tgacctcgac | tacgactcgg | tgcagccgta | tttctactgc | 120 |
| gacgaggagg | agaacttcta | ccagcagcag | cagcagagcg | agctgcagcc | cccggcgccc | 180 |
| agcgaggata | tctggaagaa | attcgagctg | ctgcccaccc | cgcccctgtc | cctagccgc | 240 |
| cgctccgggc | tctgctcgcc | ctcctacgtt | gcggtcacac | ccttctccct | cggggagac | 300 |
| aacgacggcg | gtggcgggag | cttctccacg | gccgaccagc | tggagatggt | gaccgagctg | 360 |
| ctgggaggag | acatggtgaa | ccagagtttc | atctgcgacc | cggacgacga | gaccttcatc | 420 |
| aaaaacatca | tcatccagga | ctgtatgtgg | agcggcttct | cggccgccgc | caagctcgtc | 480 |
| tcagagaagc | tggcctccta | ccaggctgcg | cgcaaagaca | gcggcagccc | gaaccccgcc | 540 |
| cgcggccaca | gcgtctgctc | cacctccagc | ttgtacctgc | aggatctgag | cgccgccgcc | 600 |
| tcagagtgca | tcgaccctc | ggtggtcttc | ccctaccctc | tcaacgacag | cagctcgccc | 660 |
| aagtcctgcg | cctcgcaaga | ctccagcgcc | ttctctccgt | cctcggattc | tctgctctcc | 720 |
| tcgacggagt | cctccccgca | gggcagcccc | gagcccctgg | tgctccatga | ggagacaccg | 780 |
| cccaccacca | gcagcgactc | tgaggaggaa | caagaagatg | aggaagaaat | cgatgttgtt | 840 |
| tctgtggaaa | agaggcaggc | tcctggcaaa | aggtcagagt | ctggatcacc | ttctgctgga | 900 |
| ggccacagca | aacctcctca | gcccactg | gtcctcaaga | ggtgccacgt | ctccacacat | 960 |
| cagcacaact | acgcagcgcc | tccctccact | cggaaggact | atcctgctgc | caagagggtc | 1020 |
| aagttggaca | gtgtcagagt | cctgagacag | atcagcaaca | accgaaaatg | caccagcccc | 1080 |
| aggtcctcgg | acaccgagga | gaatgtcaag | aggcgaacac | acaacgtctt | ggagcgccag | 1140 |
| aggaggaacg | agctaaaacg | gagctttttt | gccctgcgtg | accagatccc | ggagttggaa | 1200 |
| aacaatgaaa | aggcccccaa | ggtagttatc | cttaaaaaag | ccacagcata | catcctgtcc | 1260 |
| gtccaagcag | aggagcaaaa | gctcatttct | gaagaggact | tgttgcggaa | acgacgagaa | 1320 |
| cagttgaaac | acaaacttga | acagctacgg | aactcttgtg | cg |  | 1362 |

<210> SEQ ID NO 27
<211> LENGTH: 454
<212> TYPE: PRT
<213> ORGANISM: Homo sapiens

<400> SEQUENCE: 27

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile

```
                50                  55                  60
Trp Lys Lys Phe Glu Leu Leu Pro Thr Pro Leu Ser Pro Ser Arg
 65                  70                  75                  80

Arg Ser Gly Leu Cys Ser Pro Ser Tyr Val Ala Val Thr Pro Phe Ser
                     85                  90                  95

Leu Arg Gly Asp Asn Asp Gly Gly Gly Ser Phe Ser Thr Ala Asp
                100                 105                 110

Gln Leu Glu Met Val Thr Glu Leu Leu Gly Gly Asp Met Val Asn Gln
                115                 120                 125

Ser Phe Ile Cys Asp Pro Asp Asp Glu Thr Phe Ile Lys Asn Ile Ile
                130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Leu Tyr
                180                 185                 190

Leu Gln Asp Leu Ser Ala Ala Ala Ser Glu Cys Ile Asp Pro Ser Val
                195                 200                 205

Val Phe Pro Tyr Pro Leu Asn Asp Ser Ser Pro Lys Ser Cys Ala
210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
                260                 265                 270

Asp Glu Glu Glu Ile Asp Val Val Ser Val Glu Lys Arg Gln Ala Pro
                275                 280                 285

Gly Lys Arg Ser Glu Ser Gly Ser Pro Ser Ala Gly Gly His Ser Lys
                290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
                340                 345                 350

Asn Asn Arg Lys Cys Thr Ser Pro Arg Ser Ser Asp Thr Glu Glu Asn
                355                 360                 365

Val Lys Arg Arg Thr His Asn Val Leu Glu Arg Gln Arg Arg Asn Glu
370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
                420                 425                 430

Asp Leu Leu Arg Lys Arg Arg Glu Gln Leu Lys His Lys Leu Glu Gln
                435                 440                 445

Leu Arg Asn Ser Cys Ala
                450

<210> SEQ ID NO 28
```

<211> LENGTH: 627
<212> TYPE: DNA
<213> ORGANISM: Homo sapiens

<400> SEQUENCE: 28

```
atgggctccg tgtccaacca gcagtttgca ggtggctgcg ccaaggcggc agaagaggcg      60
cccgaggagg cgccggagga cgcggcccgg cggcggacg agcctcagct gctgcacggt     120
gcgggcatct gtaagtggtt caacgtgcgc atggggttcg gcttcctgtc catgaccgcc    180
cgcgccgggg tcgcgctcga ccccccagtg gatgtctttg tgcaccagag taagctgcac    240
atggaagggt tccggagctt gaaggagggt gaggcagtgg agttcacctt taagaagtca    300
gccaagggtc tggaatccat ccgtgtcacc ggacctggtg gagtattctg tattgggagt    360
gagaggcggc aaaaggaaa gagcatgcag aagcgcagat caaaaggaga caggtgctac    420
aactgtggag gtctagatca tcatgccaag gaatgcaagc tgccacccca gcccaagaag    480
tgccacttct gccagagcat cagccatatg gtagcctcat gtccgctgaa ggcccagcag    540
ggccctagtg cacagggaaa gccaacctac tttcgagagg aagaagaaga atccacagc    600
cctaccctgc tcccggaggc acagaat                                        627
```

<210> SEQ ID NO 29
<211> LENGTH: 209
<212> TYPE: PRT
<213> ORGANISM: Homo sapiens

<400> SEQUENCE: 29

```
Met Gly Ser Val Ser Asn Gln Gln Phe Ala Gly Gly Cys Ala Lys Ala
1               5                   10                  15

Ala Glu Glu Ala Pro Glu Glu Ala Pro Glu Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Ser
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

Cys His Phe Cys Gln Ser Ile Ser His Met Val Ala Ser Cys Pro Leu
                165                 170                 175

Lys Ala Gln Gln Gly Pro Ser Ala Gln Gly Lys Pro Thr Tyr Phe Arg
            180                 185                 190

Glu Glu Glu Glu Glu Ile His Ser Pro Thr Leu Leu Pro Glu Ala Gln
        195                 200                 205

Asn
```

<210> SEQ ID NO 30

<211> LENGTH: 1746
<212> TYPE: DNA
<213> ORGANISM: Homo sapiens

<400> SEQUENCE: 30

```
atgtctcccg ccccaagacc ctcccgttgt ctcctgctcc ccctgctcac gctcggcacc      60
gcgctcgcct ccctcggctc ggcccaaagc agcagcttca gccccgaagc ctggctacag     120
caatatggct acctgcctcc cggggaccta cgtacccaca cacagcgctc acccccagtca    180
ctctcagcgg ccatcgctgc catgcagaag ttttacggct gcaagtaaca aggcaaagct     240
gatgcagaca ccatgaaggc catgaggcgc ccccgatgtg tgttccaga  caagtttggg     300
gctgagatca aggccaatgt tcgaaggaag cgctacgcca tccagggtct caaatggcaa     360
cataatgaaa tcactttctg catccagaat tacaccccca aggtgggcga gtatgccaca     420
tacgaggcca ttcgcaaggc gttccgcgtg tgggagagtg ccacaccact gcgcttccgc     480
gaggtgccct atgcctacat ccgtgagggc catgagaagc aggccgacat catgatcttc     540
tttgccgagg gcttccatgg cgacagcacg cccttcgatg tgagggcgg cttcctggcc      600
catgcctact tcccaggccc caacattgga ggagacaccc actttgactc tgccgagcct     660
tggactgtca ggaatgagga tctgaatgga atgacatct  tcctggtggc tgtgcacgag     720
ctgggccatg ccctggggct cgagcattcc agtgacccct cggccatcat ggcacccttt     780
taccagtgga tggacacgga gaattttgtg ctgcccgatg atgaccgccg ggcatccag     840
caactttatg ggggtgagtc agggttcccc accaagatgc cccctcaacc caggactacc     900
tcccggcctt ctgttcctga taaacccaaa aaccccacct atgggcccaa catctgtgac     960
gggaactttg acaccgtggc catgctccga ggggagatgt tgtcttcaa ggagcgctgg    1020
ttctggcggg tgaggaataa ccaagtgatg atggatacc  caatgcccat ggccagttc    1080
tggcggggcc tgcctgcgtc catcaacact gcctacgaga ggaaggatgg caaattcgtc    1140
ttcttcaaag agacaagca ttgggtgttt gatgaggcgt ccctggaacc tggctacccc    1200
aagcacatta aggagctggg ccgagggctg cctaccgaca agattgatgc tgctctcttc    1260
tggatgccca atgaaagac ctacttcttc cgtggaaaca agtactaccg tttcaacgaa    1320
gagctcaggg cagtggatag cgagtacccc aagaacatca agtctggga agggatccct    1380
gagtctccca gagggtcatt catgggcagc gatgaagtct tcacttactt ctacaagggg    1440
aacaaatact ggaaattcaa caaccagaag ctgaaggtag aaccgggcta ccccaagtca    1500
gccctgaggg actggatggg ctgcccatcg ggaggccggc cggatgaggg gactgaggag    1560
gagacggagg tgatcatcat tgaggtggac gaggagggcg gcgggcggt  gagcgcggct    1620
gccgtggtgc tgcccgtgct gctgctgctc ctggtgctgg cggtgggcct tgcagtcttc    1680
ttcttcagac gccatgggac ccccaggcga ctgctctact gccagcgttc cctgctggac    1740
aaggtc                                                              1746
```

<210> SEQ ID NO 31
<211> LENGTH: 582
<212> TYPE: PRT
<213> ORGANISM: Homo sapiens

<400> SEQUENCE: 31

```
Met Ser Pro Ala Pro Arg Pro Ser Arg Cys Leu Leu Leu Pro Leu Leu
1               5                   10                  15

Thr Leu Gly Thr Ala Leu Ala Ser Leu Gly Ser Ala Gln Ser Ser Ser
            20                  25                  30
```

-continued

Phe Ser Pro Glu Ala Trp Leu Gln Gln Tyr Gly Tyr Leu Pro Pro Gly
       35                    40                      45

Asp Leu Arg Thr His Thr Gln Arg Ser Pro Gln Ser Leu Ser Ala Ala
 50                        55                      60

Ile Ala Ala Met Gln Lys Phe Tyr Gly Leu Gln Val Thr Gly Lys Ala
 65                    70                      75                      80

Asp Ala Asp Thr Met Lys Ala Met Arg Arg Pro Arg Cys Gly Val Pro
                  85                      90                      95

Asp Lys Phe Gly Ala Glu Ile Lys Ala Asn Val Arg Arg Lys Arg Tyr
                 100                    105                    110

Ala Ile Gln Gly Leu Lys Trp Gln His Asn Glu Ile Thr Phe Cys Ile
              115                    120                    125

Gln Asn Tyr Thr Pro Lys Val Gly Glu Tyr Ala Thr Tyr Glu Ala Ile
           130                    135                    140

Arg Lys Ala Phe Arg Val Trp Glu Ser Ala Thr Pro Leu Arg Phe Arg
145                    150                    155                    160

Glu Val Pro Tyr Ala Tyr Ile Arg Glu Gly His Glu Lys Gln Ala Asp
                   165                    170                    175

Ile Met Ile Phe Phe Ala Glu Gly Phe His Gly Asp Ser Thr Pro Phe
              180                    185                    190

Asp Gly Glu Gly Gly Phe Leu Ala His Ala Tyr Phe Pro Gly Pro Asn
             195                    200                    205

Ile Gly Gly Asp Thr His Phe Asp Ser Ala Glu Pro Trp Thr Val Arg
210                    215                    220

Asn Glu Asp Leu Asn Gly Asn Asp Ile Phe Leu Val Ala Val His Glu
225                    230                    235                    240

Leu Gly His Ala Leu Gly Leu Glu His Ser Ser Asp Pro Ser Ala Ile
                   245                    250                    255

Met Ala Pro Phe Tyr Gln Trp Met Asp Thr Glu Asn Phe Val Leu Pro
              260                    265                    270

Asp Asp Asp Arg Arg Gly Ile Gln Gln Leu Tyr Gly Gly Glu Ser Gly
           275                    280                    285

Phe Pro Thr Lys Met Pro Pro Gln Pro Arg Thr Thr Ser Arg Pro Ser
        290                    295                    300

Val Pro Asp Lys Pro Lys Asn Pro Thr Tyr Gly Pro Asn Ile Cys Asp
305                    310                    315                    320

Gly Asn Phe Asp Thr Val Ala Met Leu Arg Gly Glu Met Phe Val Phe
                   325                    330                    335

Lys Glu Arg Trp Phe Trp Arg Val Arg Asn Asn Gln Val Met Asp Gly
              340                    345                    350

Tyr Pro Met Pro Ile Gly Gln Phe Trp Arg Gly Leu Pro Ala Ser Ile
           355                    360                    365

Asn Thr Ala Tyr Glu Arg Lys Asp Gly Lys Phe Val Phe Phe Lys Gly
370                    375                    380

Asp Lys His Trp Val Phe Asp Glu Ala Ser Leu Glu Pro Gly Tyr Pro
385                    390                    395                    400

Lys His Ile Lys Glu Leu Gly Arg Gly Leu Pro Thr Asp Lys Ile Asp
                   405                    410                    415

Ala Ala Leu Phe Trp Met Pro Asn Gly Lys Thr Tyr Phe Phe Arg Gly
              420                    425                    430

Asn Lys Tyr Tyr Arg Phe Asn Glu Glu Leu Arg Ala Val Asp Ser Glu
           435                    440                    445

```
Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Thr Glu Val Ile Ile Glu
        515                 520                 525

Val Asp Glu Glu Gly Gly Gly Ala Val Ser Ala Ala Ala Val Val Leu
    530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
            580

<210> SEQ ID NO 32
<211> LENGTH: 1821
<212> TYPE: DNA
<213> ORGANISM: Homo sapiens

<400> SEQUENCE: 32
atgatcttac tcacattcag cactggaaga cggttggatt tcgtgcatca ttcgggggtg      60 ttttcttgc  aaaccttgct ttggatttta tgtgctacag tctgcggaac ggagcagtat     120
ttcaatgtgg aggtttggtt acaaaagtac ggctaccttc caccgactga ccccagaatg     180
tcagtgctgc gctctgcaga gaccatgcag tctgccctag ctgccatgca gcagttctat     240
ggcattaaca tgacaggaaa agtggacaga aacacaattg actggatgaa gaagccccga     300
tgcggtgtac ctgaccagac aagaggtagc tccaaatttc atattcgtcg aaagcgatat     360
gcattgacag acagaaatg  gcagcacaag cacatcactt acagtataaa gaacgtaact     420
ccaaaagtag gagaccctga ctcgtaaa   gctattcgcc gtgcctttga tgtgtggcag     480
aatgtaactc ctctgacatt tgaagaagtt ccctacagtg aattagaaaa tggcaaacgt     540
gatgtggata taaccattat ttttgcatct ggtttccatg gggacagctc tccctttgat     600
ggagagggag gattttggc  acatgcctac ttccctggac caggaattgg aggagatacc     660
cattttgact cagatgagcc atggacacta ggaaatccta atcatgatgg aaatgactta     720
tttcttgtag cagtccatga actgggacat gctctgggat tggagcattc aatgaccccc     780
actgccatca tggctccatt ttaccagtac atggaaacag caacttcaa  actacctaat     840 gatgatttac agggcatcca gaaaatatat ggtccacctg acaagattcc tccacctaca     900
agacctctac cgacagtgcc cccacaccgc tctattcctc cggctgaccc aaggaaaaat     960
gacaggccaa aacctcctcg gcctccaacc ggcagaccct cctatcccgg agccaaaccc    1020
aacatctgtg atgggaactt taacactcta gctattcttc gtcgtgagat gtttgtttc    1080 aaggaccagt ggttttggcg agtgagaaac aacagggtga tggatggata cccaatgcaa    1140
attacttact tctggcgggg cttgcctcct agtatcgatg cagtttatga aaatagcgac    1200 gggaatttg  tgttctttaa aggtaacaaa tattgggtgt tcaaggatac aactcttcaa    1260
cctggttacc ctcatgactt gataaccctt ggaagtggaa ttccccctca tggtattgat    1320
```

-continued

```
tcagccattt ggtgggagga cgtcgggaaa acctatttct tcaagggaga cagatattgg    1380
agatatagtg aagaaatgaa acaatggac cctggctatc ccaagccaat cacagtctgg    1440
aaagggatcc ctgaatctcc tcagggagca tttgtacaca agaaaatgg ctttacgtat    1500 ttctacaaag gaaggagta ttggaaattc aacaaccaga tactcaaggt agaacctgga    1560
catccaagat ccatcctcaa ggattttatg gctgtgatg gaccaacaga cagagttaaa    1620
gaaggacaca gcccaccaga tgatgtagac attgtcatca aactggacaa cacagccagc    1680
actgtgaaag ccatagctat tgtcattccc tgcatcttgg ccttatgcct ccttgtattg    1740
gtttacactg tgttccagtt caagaggaaa ggaacacccc gccacatact gtactgtaaa    1800
cgctctatgc aagagtgggt g                                              1821
```

<210> SEQ ID NO 33
<211> LENGTH: 607
<212> TYPE: PRT
<213> ORGANISM: Homo sapiens

<400> SEQUENCE: 33

```
Met Ile Leu Leu Thr Phe Ser Thr Gly Arg Arg Leu Asp Phe Val His
1               5                   10                  15

His Ser Gly Val Phe Phe Leu Gln Thr Leu Leu Trp Ile Leu Cys Ala
            20                  25                  30

Thr Val Cys Gly Thr Glu Gln Tyr Phe Asn Val Glu Val Trp Leu Gln
        35                  40                  45

Lys Tyr Gly Tyr Leu Pro Pro Thr Asp Pro Arg Met Ser Val Leu Arg
    50                  55                  60

Ser Ala Glu Thr Met Gln Ser Ala Leu Ala Ala Met Gln Gln Phe Tyr
65                  70                  75                  80

Gly Ile Asn Met Thr Gly Lys Val Asp Arg Asn Thr Ile Asp Trp Met
                85                  90                  95

Lys Lys Pro Arg Cys Gly Val Pro Asp Gln Thr Arg Gly Ser Ser Lys
            100                 105                 110

Phe His Ile Arg Arg Lys Arg Tyr Ala Leu Thr Gly Gln Lys Trp Gln
        115                 120                 125

His Lys His Ile Thr Tyr Ser Ile Lys Asn Val Thr Pro Lys Val Gly
    130                 135                 140

Asp Pro Glu Thr Arg Lys Ala Ile Arg Arg Ala Phe Asp Val Trp Gln
145                 150                 155                 160

Asn Val Thr Pro Leu Thr Phe Glu Glu Val Pro Tyr Ser Glu Leu Glu
                165                 170                 175

Asn Gly Lys Arg Asp Val Asp Ile Thr Ile Ile Phe Ala Ser Gly Phe
            180                 185                 190

His Gly Asp Ser Ser Pro Phe Asp Gly Glu Gly Gly Phe Leu Ala His
        195                 200                 205

Ala Tyr Phe Pro Gly Pro Gly Ile Gly Gly Asp Thr His Phe Asp Ser
    210                 215                 220

Asp Glu Pro Trp Thr Leu Gly Asn Pro Asn His Asp Gly Asn Asp Leu
225                 230                 235                 240

Phe Leu Val Ala Val His Glu Leu Gly His Ala Leu Gly Leu Glu His
                245                 250                 255

Ser Asn Asp Pro Thr Ala Ile Met Ala Pro Phe Tyr Gln Tyr Met Glu
            260                 265                 270

Thr Asp Asn Phe Lys Leu Pro Asn Asp Asp Leu Gln Gly Ile Gln Lys
        275                 280                 285
```

Ile Tyr Gly Pro Pro Asp Lys Ile Pro Pro Thr Arg Pro Leu Pro
290                 295                 300

Thr Val Pro Pro His Arg Ser Ile Pro Pro Ala Asp Pro Arg Lys Asn
305                 310                 315                 320

Asp Arg Pro Lys Pro Arg Pro Pro Thr Gly Arg Pro Ser Tyr Pro
            325                 330                 335

Gly Ala Lys Pro Asn Ile Cys Asp Gly Asn Phe Asn Thr Leu Ala Ile
            340                 345                 350

Leu Arg Arg Glu Met Phe Val Phe Lys Asp Gln Trp Phe Trp Arg Val
            355                 360                 365

Arg Asn Asn Arg Val Met Asp Gly Tyr Pro Met Gln Ile Thr Tyr Phe
370                 375                 380

Trp Arg Gly Leu Pro Pro Ser Ile Asp Ala Val Tyr Glu Asn Ser Asp
385                 390                 395                 400

Gly Asn Phe Val Phe Phe Lys Gly Asn Lys Tyr Trp Val Phe Lys Asp
                405                 410                 415

Thr Thr Leu Gln Pro Gly Tyr Pro His Asp Leu Ile Thr Leu Gly Ser
            420                 425                 430

Gly Ile Pro Pro His Gly Ile Asp Ser Ala Ile Trp Trp Glu Asp Val
            435                 440                 445

Gly Lys Thr Tyr Phe Phe Lys Gly Asp Arg Tyr Trp Arg Tyr Ser Glu
450                 455                 460

Glu Met Lys Thr Met Asp Pro Gly Tyr Pro Lys Pro Ile Thr Val Trp
465                 470                 475                 480

Lys Gly Ile Pro Glu Ser Pro Gln Gly Ala Phe Val His Lys Glu Asn
                485                 490                 495

Gly Phe Thr Tyr Phe Tyr Lys Gly Lys Glu Tyr Trp Lys Phe Asn Asn
            500                 505                 510

Gln Ile Leu Lys Val Glu Pro Gly His Pro Arg Ser Ile Leu Lys Asp
            515                 520                 525

Phe Met Gly Cys Asp Gly Pro Thr Asp Arg Val Lys Glu Gly His Ser
530                 535                 540

Pro Pro Asp Asp Val Asp Ile Val Ile Lys Leu Asp Asn Thr Ala Ser
545                 550                 555                 560

Thr Val Lys Ala Ile Ala Ile Val Ile Pro Cys Ile Leu Ala Leu Cys
                565                 570                 575

Leu Leu Val Leu Val Tyr Thr Val Phe Gln Phe Lys Arg Lys Gly Thr
            580                 585                 590

Pro Arg His Ile Leu Tyr Cys Lys Arg Ser Met Gln Glu Trp Val
            595                 600                 605

<210> SEQ ID NO 34
<211> LENGTH: 31
<212> TYPE: PRT
<213> ORGANISM: Artificial Sequence
<220> FEATURE:
<223> OTHER INFORMATION: Nonsense polypeptide for control

<400> SEQUENCE: 34

His His His His His His Ser Ser Ser Gly Ser Ser Ser Ser Gly
1               5                   10                  15

Ser Ser Ser Ser Gly Gly Arg Gly Asp Ser Gly Arg Gly Asp Ser
            20                  25                  30

METHOD FOR MAINTAINING PLURIPOTENCY IN CELLS

CROSS-REFERENCE TO RELATED APPLICATIONS

The present application claims the benefit of U.S. Provisional Patent Application No. 61/104,231, filed Oct. 9, 2008, the contents of which are incorporated by reference in their entirety.

BACKGROUND OF THE INVENTION

1. Field of the Invention

The present application relates to the field of inducing pluripotency in cells.

2. General Background and State of the Art

It has been demonstrated, in mouse and human, that somatic cells can be reprogrammed by ectopic expression of transcription factors (Lowry et al., 2008; Maherali et al., 2007; Nakagawa et al., 2008; Okita et al., 2007; Park et al., 2008; Takahashi et al., 2006; Takahashi and Yamanaka, 2006; Wernig et al., 2007; Yu et al., 2006) to become pluripotent. The generation of induced pluripotent stem (iPS) cells holds great promise for the realization of truly personalized regenerative medicine (Yamanaka, 2007; Jaenish and Young, 2008) because stem cells derived from a patient's own skin cell can be used to generate cells and tissues to repair damage caused by disease or aging. Forced expression of combinations of the transcription factors, Oct4, Sox2, Klf4 and c-Myc or Oct4, Sox2, Nanog and Lin28 have been shown to cause mature cells to revert to the pluripotent state.

In earlier studies, the transcription factors were expressed using multiple viral vectors (Takahashi and Yamanaka, 2006; Okita et al., 2007; Maherali et al., 2007; Wernig et al., 2007; Takahashi et al., 2006; Yu et al., 2006; Park et al., 2008). The use of multiple vectors presented a problem because of multiple integration events, which could lead to increased risk of oncogenicity (Takahashi and Yamanaka, 2006; Aoi et al., 2008). Researchers have tried to overcome this problem by using single vector systems (Sommer et al., 2009), excisable vectors (Kaji et al., 2009; Soldner et al., 2009; Woltjen et al., 2009), non-integrating vectors (Stadtfeld et al., 2009; Yu et al., 2009) and transient transfections (Okita et al., 2009). However, these methods are extremely inefficient at achieving epigenetic reprogramming.

Methods for inducing pluripotency include transfection of the oncogene c-Myc, which is undesirable because of its potential to cause cancer. iPS cells can be generated without transfecting c-Myc (Nakagawa et al., 2008; Wernig et al., 2008). However, the efficiency of reprogramming was greatly decreased. Similarly, Klf4 can induce dysplasia (Foster et al., 2005).

Because of the problems associated with multiple viral vector integration and undesirable side effects of some of the genes that induce pluripotency, there is a need to replace the use of some or all of the pluripotency-inducing genes with the protein gene products and proteins that regulate their expression or whose expression is regulated by the pluripotency-inducing genes or small molecules that regulate the expression of genes or proteins that induce pluripotency. To this end, it has been reported that the introduction of the gene products, rather than the genes, also induced pluripotency (Zhou et al., 2009). Recombinant Oct4, Sox2, Klf4 and c-Myc, tagged with poly-arginine to facilitate entry into the cell, reprogrammed mouse somatic cells. Others have used small molecules to replace the need for one of the genes of the core set. A small molecule that upregulated Nanog eliminated the need for the Klf4 gene, which also upregulates Nanog (Lyssiotis et al., 2009). In another study, a small molecule HDAC inhibitor removed the requirement for both Klf4 and c-Myc (Huangfu et al., 2008, a&b). These studies show that: 1) the protein gene products can replace the need for the genes; 2) small molecules that upregulate genes can replace the need for the genes; and 3) genes (or gene products) in the same regulatory pathway can substitute for one another.

Despite these achievements, a major problem that remains is that these methods suffer from low efficiency of reprogramming. Current rates of inducing pluripotency in somatic cells are so low that they make therapeutic uses of iPS cells impractical. Therefore, what is needed is to identify proteins and small molecules that either alone or in addition to those already identified, induce pluripotency or improve the efficiency of the induction of pluripotency in cells.

SUMMARY OF THE INVENTION

In one aspect, the present invention is directed to a method for inducing or maintaining pluripotency in a cell comprising contacting the cell with a biological or chemical species that increases MUC1* activity. The biological species may be a gene or a protein. The protein may be preferably a MUC1* ligand, preferably the ligand is NM23. The protein may also be an antibody, preferably bi-valent antibody that specifically recognizes the PSMGFR sequence of MUC1*. In another aspect, the chemical species may be a small molecule. Preferably, the small molecule may enhance the transcription of MUC1, its cleavage enzyme, or NM23. Preferably, the cleavage enzyme may be MMP-16, MMP-14 or ADAM-17. Further, the small molecule may enhance cleavage of MUC1. The small molecule may be a phorbol ester.

In another aspect, the gene above may encode MUC1 or MUC1*, or an effective fragment thereof, or a ligand of MUC1*, such as but not limited to a MUC1* antibody or NM23. Preferably, the fragment may be the cytoplasmic tail of MUC1 or MUC1*

In further other aspects, the invention is directed to contacting the cell with an additional molecule that increases expression of gene products that induce pluripotency, such as but not limited to a molecule that increases expression of OCT4, SOX2, NANOG, KLF4 or LIN28, preferably of OCT4, and SOX2.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

Figure 1A:
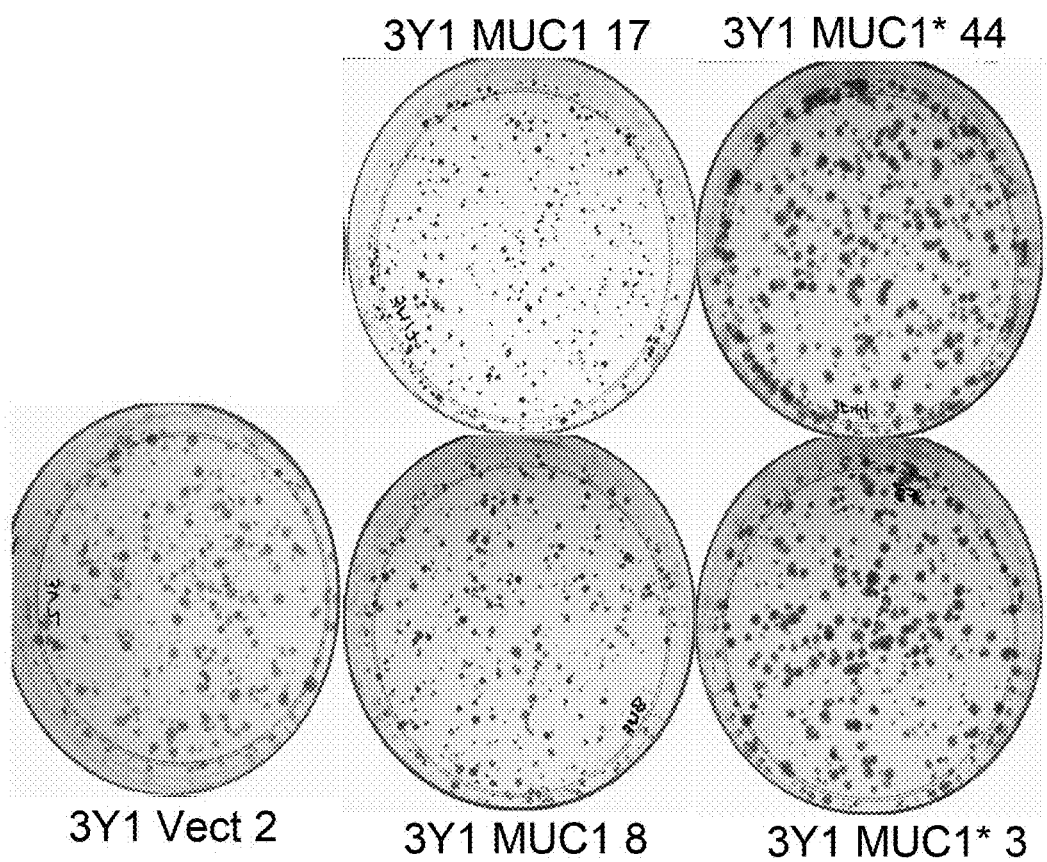
FIGS. 1A-1F show that MUC1* increases growth rate. A. Clonogenic assay shows that transfecting rat fibroblasts (3Y1) with MUC1* increases growth rate but MUC1 (full-length) does not; B. MUC1* activity increases survival.

Breast cancer cells that have acquired resistance to TAXOL® do so by increasing MUC1* expression. Treatment with anti-MUC1* Fab reverses acquired resistance to TAXOL®-induced cell death; C. Ligand-induced dimerization of MUC1* extracellular domain stimulates growth. The addition of bivalent anti-MUC1* antibodies stimulates the growth of MUC1*-positive cells. Blocking with the anti-MUC1* (mv) Fab inhibits cell growth. Bell-shaped growth curve is characteristic of receptor dimerization. Growth of control MUC1-negative HEK 293 cells was not affected; D. Suppression of MUC1*, using specific siRNA, abolishes the growth stimulatory effects of adding a MUC1* dimerizing ligand; E. NM23 is the native MUC1* activating ligand. NM23 stimulates growth of MUC1*-positive cancer cells and produces bell-shaped curve indicative of receptor dimerizatio. Effect is abolished by siRNA suppression of MUC1; F. Direct binding of NM23 to the MUC1* peptide is detected by SPR. 15 nM NM23 binds to MUC1* extracellular domain peptide but not to irrelevant peptide. Measurements were done using SPR (surface plasmon resonance) and NTA-Ni-SAM coated Au chips.

FIGS. 2A-2F show that MUC1 is cleaved on undifferentiated hESCs but MUC1 is not cleaved on differentiated hESCs. Immunocytochemistry shows that undifferentiated (pluripotent) stem cells express MUC1* and not the full-length protein; OCT4 is the gold standard marker for pluripotency. All pluripotent stem cells are MUC1*-positive. However, as soon as differentiation initiates (loss of OCT4 expression), cleavage stops and only full-length MUC1 (MUC1-FL) is detected. Panels A-C are photos of the same undifferentiated stem cell colony stained with: A. anti-MUC1* antibody that recognizes the PSMGFR peptide; B. anti-OCT4; C. anti-MUC1 full-length VU4H5. Panels D-F are photos of the same newly differentiated stem cell colony stained with: D. anti-MUC1* antibody that recognizes the PSMGFR peptide; E. anti-OCT4; F. anti-MUC1 full-length VU4H5.

FIG. 3A-3F shows that NM23 (MUC1* ligand) co-localizes with MUC1* and OCT4 on undifferentiated hESCs, but not on differentiated cells. Immunocytochemistry shows that undifferentiated (pluripotent) stem cells express MUC1* and its activating ligand NM23. However, when stem cells begin to differentiate (loss of OCT4 expression), then MUC1 is expressed as the full-length protein and NM23 is no longer secreted. Dotted lines indicate the border between the undifferentiated and the newly differentiating portions. Panels A-C are photos of the same undifferentiated stem cell colony stained with: A. an antibody that recognizes NM23; B. anti-MUC1* antibody that recognizes the PSMGFR peptide; C. an overlay of (A), (B) and the same cells stained with DAPI to stain nuclei. Panels D-F are photos of the same undifferentiated stem cell colony stained with: D. an antibody that recognizes NM23; E. an antibody that recognizes OCT4; F. an overlay of (D), (E) and the same cells stained with DAPI to stain nuclei.

FIGS. 4A-4H show that stimulation of MUC1* promotes growth and inhibits differentiation of hESCs in the absence of bFGF and conditioned media. Ligand-induced dimerization of MUC1* extracellular domain produced, using bivalent anti-MUC1* antibody, essentially 100% pluripotent colonies after 5 weeks growth in minimal media without adding bFGF or conditioned media. Colonies were grown on MATRIGEL. The same results were obtained when NM23 or NM23 S120G mutant was used to activate MUC1*. Panels A-D are photos of wells where cell growth medium was supplemented with conditioned medium from fibroblast feeder cells plus either anti-MUC1* or bFGF. Panels E-H are photos of wells where stem cells were cultured in minimal medium plus either anti-MUC1* or bFGF. Images are of cells stained with: A. antibody that recognizes OCT4; B. DAPI staining of cells of (A); C. anti-MUC1*; D. DAPI staining of cells of (C); E. antibody that recognizes OCT4; F. DAPI staining of cells of (E); G. anti-MUC1*; H. DAPI staining of cells of (G).

Figure 5:
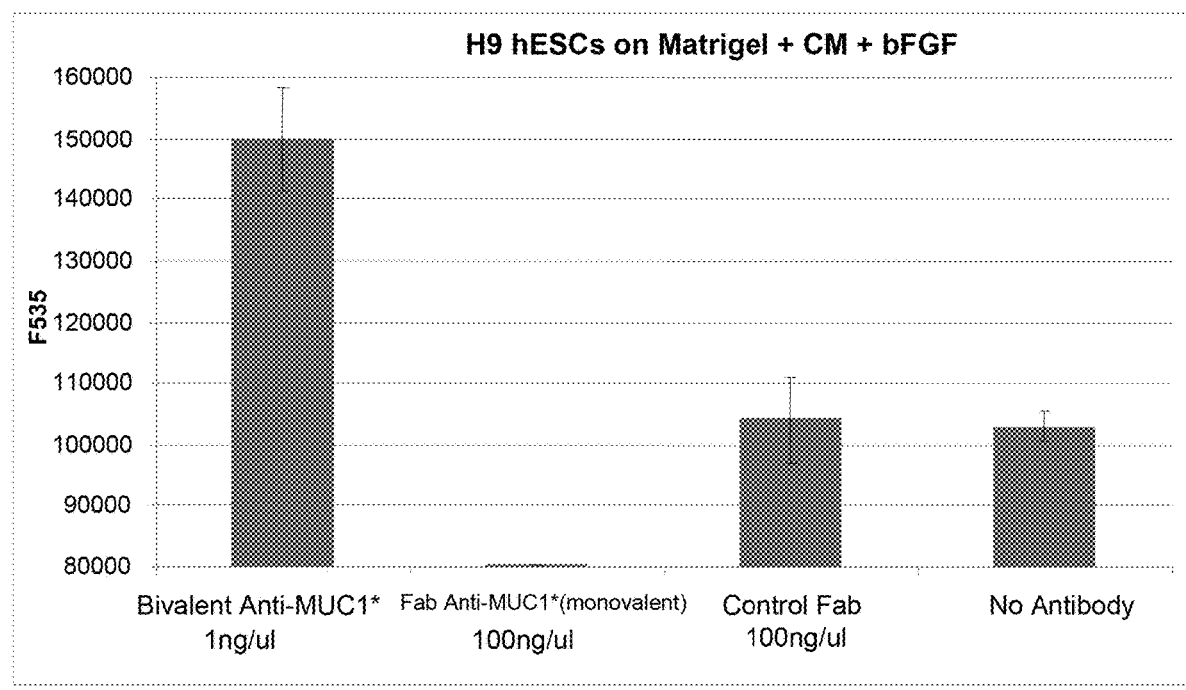

FIG. 5 shows a bar graph indicating that MUC1* activity is required for pluripotent stem cell growth. Blocking MUC1* with anti-MUC1* Fab caused total stem cell death within 8-12 hours even though bFGF and conditioned media (CM) was present. Bivalent anti-MUC1* stimulated growth. Cells cultured 25 hrs; live cells were measured in a Calcein fluorescent assay.

FIGS. 6A-6B show photos evidencing that MUC1* translocates to the nucleus of cells. A MUC1* Fab was fluorescently labeled (red) then incubated with MUC1*-positive cells. The photos show that, initially, MUC1* is uniformly distributed on the cell surface. However, after 40 minutes, MUC1* is concentrated in the nucleus. For comparison cells were also stained with a fluorescently labeled antibody (green) that recognizes EEA1, which remains uniformly distributed in cytoplasm throughout the experiment. A. photo of cells taken at time zero; B. photo of cells taken 40 minutes after the addition of the Fab of anti-MUC1*.

DETAILED DESCRIPTION OF THE PREFERRED EMBODIMENTS

In the present application, "a" and "an" are used to refer to both single and a plurality of objects.

As used herein, "increasing MUC1* activity" refers to directly or indirectly increasing MUC1* signaling, and includes without limitation the dimerization of MUC1* receptor and also increased production of MUC1* by cleavage of the MUC1 receptor. MUC1* activity may be also increased by higher transcriptional expression of MUC1 receptor, which is further cleaved and dimerized. Therefore, in one aspect, MUC1* activity may be increased by a higher activity of the effector molecule that dimerizes MUC1*, or the higher activity of the cleavage molecule that cleaves MUC1 so that MUC1* is formed, or increased expression of the MUC1. Therefore, any chemical or biological species that is able to increase the activity of the MUC1* dimerizing ligand, MUC1 cleavage enzyme to form MUC1*, or any transcriptional activator that enhances expression of MUC1, is encompassed as a species that "increases MUC1* activity".

As used herein, "MUC1 Growth Factor Receptor" (MGFR) is a functional definition meaning that portion of the MUC1 receptor that interacts with an activating ligand, such as a growth factor or a modifying enzyme such as a cleavage enzyme. The MGFR region of MUC1 is that extracellular portion that is closest to the cell surface and is defined by most or all of the PSMGFR, as defined below. The MGFR is inclusive of both unmodified peptides and peptides that have undergone enzyme modifications, such as, for example, phosphorylation, glycosylation and so forth.

As used herein, "Primary Sequence of the MUC1 Growth Factor Receptor" (PSMGFR) refers to peptide sequence that defines most or all of the MGFR in some cases, and functional variants and fragments of the peptide sequence. The PSMGFR is defined as SEQ ID NO:6, and all functional variants and fragments thereof having any integer value of amino acid substitutions up to 20 (i.e. 1, 2, 3, 4, 5, 6, 7, 8, 9, 10, 11, 12, 13, 14, 15, 16, 17, 18, 19, or 20) and/or any integer value of amino acid additions or deletions up to 20 at its N-terminus and/or C-terminus. A "functional variant or fragment" in the above context refers to such variant or fragment having the ability to specifically bind to, or otherways specifically interact with, ligands that specifically bind to, or otherwise specifically interact with, the peptide of SEQ ID NO:6, while not binding strongly to identical regions of other peptide molecules identical to themselves, such that the peptide molecules would have the ability to aggregate (i.e. self-aggregate) with other identical peptide molecules. One example of a PSMGFR that is a functional variant of the PSMGFR peptide of SEQ NO:6 is SEQ ID NO:8, which differs from SEQ ID NO:6 by including an -SPY- sequence instead of the -SRY-.

As used herein, "MUC1*" refers to the MUC1 protein with the N-terminus truncated such that the extracellular domain is essentially comprised of the PSMGFR (SEQ ID NO:5).

As used herein "MUC1* associated factors" refers to agents that modify, activate, modulate the activity of, or modulate the expression of MUC1*. MUC1* associated factors include, without limitation, agents that affect dimerization of MUC1* receptor, increased production of MUC1*, induce cleavage of the MUC1 receptor, agents that increase MUC1* activity by higher transcriptional expression of MUC1 receptor, which is further cleaved and dimerized.

As used herein, "effective amount" is an amount sufficient to effect beneficial or desired clinical or biochemical results. An effective amount can be administered one or more times. For purposes of this invention, an effective amount of an inhibitor compound is an amount that is sufficient to induce or maintain pluripotency of a cell or activate MUC1*

As used herein, "fragments" or "functional derivatives" refers to biologically active amino acid sequence variants and fragments of the native ligands or receptors of the present invention, as well as covalent modifications, including derivatives obtained by reaction with organic derivatizing agents, post-translational modifications, derivatives with nonproteinaceous polymers, and immunoadhesins.

As used herein, "ligand" refers to any molecule or agent, or compound that specifically binds covalently or transiently to a molecule such as a polypeptide. When used in certain context, ligand may include antibody. In other context, "ligand" may refer to a molecule sought to be bound by another molecule with high affinity, such as but not limited to a natural or unnatural ligand for MUC1* or a cleaving enzyme binding to MUC1 or MUC1* or a dimerizing ligand for MUC1*.

As used herein, the term "specifically binds" refers to a non-random binding reaction between two molecules, for example between an antibody molecule immunoreacting with an antigen, or a non-antibody ligand reacting with another polypeptide, such as NM23 specifically binding with MUC1* or an antibody binding to MUC1* or a cleaving enzyme binding to MUC1 or MUC1*

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

```
                                              (SEQ ID NO: 1)
MTPGTQSPFF LLLLLTVLTV VTGSGHASST PGGEKETSAT
QRSSVPSSTE KNAVSMTSSV LSSHSPGSGS STTQGQDVTL
APATEPASGS AATWGQDVTS VPVTRPALGS TTPPAHDVTS
APDNKPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDNRPALGS TAPPVHNVTS
ASGSASGSAS TLVHNGTSAR ATTTPASKST PFSIPSHHSD
TPTTLASHST KTDASSTHHS SVPPLTSSNH STSPQLSTGV
SFFFLSFHIS NLQFNSSLED PSTDYYQELQ RDISEMFLQI
YKQGGFLGLS NIKFRPGSVV VQLTLAFREG TINVHDVETQ
FNQYKTEAAS RYNLTISDVS VSDVPFPFSA QSGAGVPGWG
IALLVLVCVL VALAIVYLIA LAVCQCRRKN YGQLDIFPAR
DTYHPMSEYP TYHTHGRYVP PSSTDRSPYE KVSAGNGGSS
LSYTNPAVAA ASANL
describes full-length MUC1 Receptor (Mucin 1
precursor, Genbank Accession number: P15941).

(SEQ ID NO: 2)
MTPGTQSPFFLLLLLTVLT (SEQ ID NO: 3)
MTPGTQSPFFLLLLLTVLT VVTA (SEQ ID NO: 4)
MTPGTQSPFFLLLLLTVLT VVTG
SEQ ID NOS: 2, 3 and 4 describe N-terminal MUC-1
signaling sequence for directing MUC1 receptor and
truncated isoforms to cell membrane surface. Up to
3 amino acid residues may be absent at C-terminal
end as indicated by variants in SEQ ID NOS: 2, 3
and 4.

(SEQ ID NO: 5)
GTINVHDVETQFNQYKTEAASRYNLTISDVSVSDVPFPFSAQSGAGVPGW
GIALLVLVCVLVALAIVYLIALAVCQCRRKNYGQLDIFPARDTYHPMSEY
PTYHTHGRYVPPSSTDRSPYEKVSAGNGGSSLSYTNPAVAAASANL
describes a truncated MUC1 receptor isoform having
nat-PSMGFR at its N-terminus and including the
transmembrane and cytoplasmic sequences of a full-
length MUC1 receptor.
```

(SEQ ID NO: 6)
GTINVHDVETQFNQYKTEAASRYNLTISDVSVSDVPFPFSAQSGA
describes Native Primary Sequence of the MUC1
Growth Factor Receptor (nat-PSMGFR - an example of
"PSMGFR"):

(SEQ ID NO: 7)
TINVHDVETQFNQYKTEAASRYNLTISDVSVSDVPFPFSAQSGA
describes Native Primary Sequence of the MUC1
Growth Factor Receptor (nat-PSMGFR - An example
of "PSMGFR"), having a single amino acid deletion
at the N-terminus of SEQ ID NO: 6).

(SEQ ID NO: 8)
GTINVHDVETQFNQYKTEAASPYNLTISDVSVSDVPFPFSAQSGA
describes "SPY" functional variant of the native
Primary Sequence of the MUC1 Growth Factor
Receptor having enhanced stability (var-PSMGFR -
An example of "PSMGFR").

(SEQ ID NO: 9)
TINVHDVETQFNQYKTEAASPYNLTISDVSVSDVPFPFSAQSGA
describes "SPY" functional variant of the native
Primary Sequence of the MUC1 Growth Factor
Receptor having enhanced stability (var-PSMGFR -
An example of "PSMGFR"), having a single amino
acid deletion at the C-terminus of SEQ ID NO: 8).

(SEQ ID NO: 10)
tgtcagtgccgccgaaagaactacggggcagctggacatctttccagcccg
ggatacctaccatcctatgagcgagtaccccacctaccacacccatgggc
gctatgtgcccctagcagtaccgatcgtagccctatgagaaggtttct
gcaggtaacggtggcagcagcctctcttacacaaacccagcagtggcagc
cgctctgccaacttg
describes MUC1 cytoplasmic domain nucleotide
sequence.

(SEQ ID NO: 11)
CQCRRKNYGQLDIFPARDTYHPMSEYPTYHTHGRYVPPSSTDRSPYEKVS
AGNGGSSLSYTNPAVAAASANL
describes MUC1 cytoplasmic domain amino acid
sequence.

(SEQ ID NO: 12)
gagatcctgagacaatgaatcatagtgaaagattcgttttcattgcagag
tggtatgatccaaatgcttcacttcctcgacgttatgagctttattta
cccaggggatggatctgttgaaatgcatgatgtaaagaatcatcgcacct
ttttaaagcggaccaaatatgataacctgcacttggaagatttatttata
ggcaacaaagtgaatgtcttttctcgacaactggtattaattgactatgg
ggatcaatatacagctcgccagctgggcagtaggaaagaaaaaacgctag
ccctaattaaaccagatgcaatatcaaaggctggagaaataattgaaata
ataaacaaagctggatttactataaccaaactcaaaatgatgatgctttc
aaggaaagaagcattggattttcatgtagatcaccagtcaagaccctttt
tcaatgagctgatccagtttattacaactggtcctatttactgccatggag
attttaagagatgatgctatatgtgaatggaaaagactgctgggacctgc
aaactctggagtggcacgcacagatgcttctgaaagcattagagccctct
ttggaacagatggcataagaaatgcagcgcatggcccctgattcttttgct
tctgcggccagagaaatggagttgtttttttccttcaagtggaggttgtgg
gccggcaaacactgctaaatttactaattgtacctgttgcattgttaaac
cccatgctgtcagtgaaggtatgttgaatacactatattcagtacatttt
gttaataggagagcaatgtttattttcttgatgtactttatgtatagaaa
ataa
describes NME7 nucleotide sequence (NME7: GENBANK
ACCESSION AB209049).

(SEQ ID NO: 13)
DPETMNHSERFVFIAEWYDPNASLLRRYELLFYPGDGSVEMHDVKNHRTF
LKRTKYDNLHLEDLFIGNKVNVFSRQLVLIDYGDQYTARQLGSRKEKTLA
LIKPDAISKAGEIIEIINKAGFTITKLKMMMLSRKEALDFHVDHQSRPFF
NELIQFITTGPIIAMEILRDDAICEWKRLLGPANSGVARTDASESIRALF
GTDGIRNAAHGPDSFASAAREMELFFPSSGGCGPANTAKFTNCTCCIVKP
HAVSEGMLNTLYSVHFVNRRAMFIFLMYFMYRK
describes NME7 amino acid sequence (NME7:
GENBANK ACCESSION AB209049).

(SEQ ID NO: 14)
atggtgctactgtctactttagggatcgtctttcaaggcgaggggcctcc
tatctcaagctgtgatacaggaaccatggccaactgtgagcgtaccttca
ttgcgatcaaaccagatggggtccagcggggtcttgtgggagagattatc
aagcgttttgagcagaaaggattccgccttgttggtctgaaattcatgca agcttccgaagatcttctcaaggaacactacgttgacctgaaggaccgtc
cattctttgccggcctggtgaaatacatgcactcagggccggtagttgcc
atggtctgggaggggctgaatgtggtgaagacgggccgagtcatgctcgg
ggagaccaaccctgcagactccaagcctgggaccatccgtggagacttct
gcatacaagttggcaggaacattatacatggcagtgattctgtggagagt
gcagagaaggagatcggcttgtggttttcaccctgaggaactggtagatta
cacgagctgtgctcagaactggatctatgaatga
describes NM23-H1 nucleotide sequence (NM23-H1:
GENBANK ACCESSION AF487339).

(SEQ ID NO: 15)
MVLLSTLGIVFQGEGPPISSCDTGTMANCERTFIAIKPDGVQRGLVGEII
KRFEQKGFRLVGLKFMQASEDLLKEHYVDLKDRPPFAGLVKYMHSGPVVA
MVWEGLNVVKTGRVMLGETNPADSKPGTIRGDFCIQVGRNIIHGSDSVES
AEKEIGLWFHPEELVDYTSCAQNWIYE
NM23-H1 describes amino acid sequence (NM23-H1:
GENBANK ACCESSION AF487339).

(SEQ ID NO: 16)
atggtgctactgtctactttagggatcgtctttcaaggcgaggggcctcc
tatctcaagctgtgatacaggaaccatggccaactgtgagcgtaccttca
ttgcgatcaaaccagatggggtccagcggggtcttgtgggagagattatc
aagcgttttgagcagaaaggattccgccttgttggtctgaaattcatgca
agcttccgaagatcttctcaaggaacactacgttgacctgaaggaccgtc
cattctttgccggcctggtgaaatacatgcactcagggccggtagttgcc
atggtctgggaggggctgaatgtggtgaagacgggccgagtcatgctcgg
ggagaccaaccctgcagactccaagcctgggaccatccgtggagacttct
gcatacaagttggcaggaacattatacatggcggtgattctgtggagagt
gcagagaaggagatcggcttgtggttttcaccctgaggaactggtagatta
cacgagctgtgctcagaactggatctatgaatga
describes NM23-H1 S120G mutant nucleotide sequence
(NM23-H1: GENBANK ACCESSION AF487339).

(SEQ ID NO: 17)
MVLLSTLGIVFQGEGPPISSCDTGTMANCERTFIAIKPDGVQRGLVGEII
KRFEQKGFRLVGLKFMQASEDLLKEHYVDLKDRPPFAGLVKYMHSGPVVA
MVWEGLNVVKTGRVMLGETNPADSKPGTIRGDFCIQVGRNIIHGGDSVES
AEKEIGLWFHPEELVDYTSCAQNWIYE
describes NM23-H1 S120G mutant amino acid sequence
(NM23-H1: GENBANK ACCESSION AF487339).

(SEQ ID NO: 18)
atg tacaacatga tggagacgga gctgaagccg ccgggcccgc
agcaaacttc gggggggcggc ggcggcaact ccaccgcggc
ggcggccggc ggcaaccaga aaaacagccc ggaccgcgtc
aagcggccca tgaatgcctt catggtgtgg tcccgcgggc
agcggcgcaa gatggcccag gagaacccca agatgcacaa
ctcggagatc agcaagcgcc tgggcgccga gtggaaactt
ttgtcggaa cggagaagcg gccgttcatc gacgaggcta
agcggctgcg agcgctgcac atgaaggagc cccggatta
taaataccgg ccccggcgga aaaccaagac gctcatgaag
aaggataagt acacgctgcc cggcgggctg ctggccccg
gcggcaatag catggcgagc ggggtcgggg tgggcgccgg
cctgggcgcg ggcgtgaacc agcgcatgga cagttacgcg
cacatgaacg gctggagcaa cggcagctac agcatgatgc
aggaccagct gggctaccccg cagcacccgg gctcaatgc
gcacggcgca gcgcagatgc agcccatgca ccgctacgac
gtgagcgccc tgcagtacaa ctccatgacc agctcgcaga
cctacatgaa cggctcgccc acctacagca tgtcctactc
gcagcagggc accccttggca tggctcttgg ctccatgggt
tcggtggtca agtccgaggc cagctccagc ccccctgtgg
ttacctcttc ctcccactcc agggcgcct gccaggccgg
ggacctccgg gacatgatca gcatgtatct ccccggcgcc
gaggtgccgg aaccgcccgc ccccagcaga cttcacatgt
cccagcacta ccagagcggc ccggtgcccg gcacggccat
taacggcaca ctgcccctct cacacatgtg a
describes SEQ ID No: 1 human SOX2 nucleotide
sequence (SOX2: GENBANK ACCESSION NM_003106).

(SEQ ID NO: 19)
MYNMMETELKPPGPQQTSGGGGGNSTAAAAGGNQKNSPDRVKRPMNAFMV
WSRGQRRKMAQENPKMHNSEISKRLGAEWKLLSETEKRPFIDEAKRLRAL
HMKEHPDYKYRPRRKTKTLMKKDKYTLPGGLLAPGGNSMASGVGVGAGLG
AGVNQRMDSYAHMNGWSNGSYSMMQDQLGYPQHPGLNAHGAAQMQPMHRY
DVSALQYNSMTSSQTYMNGSPTYSMSYSQQGTPGMALGSMGSVVKSEASS
SPPVVTSSSHSRAPCQAGDLRDMISMYLPGAEVPEPAAPSRLHMSQHYQS
GPVPGTAINGTLPLSHM
describes human SOX2 amino acid sequence (SOX2:
GENBANK ACCESSION NM_003106).

(SEQ ID NO: 20)
```
atggcgggacacctggcttcagattttgccttctcgcccctccaggtgg
tggaggtgatgggccagggggggccggagccggctggttgatcctcgga
cctgctaagcttcaaggccctcctggagggcaggaatcgggccgggg
gttgggccaggctctgaggtgtggggggattccccagtgccccccgccgta
tgagttctgtgggggatggcgtactgtgggccccaggttggagtgggc
tagtgcccaaggcggcttggagacctctcagcctgagggcgaagcagga
gtcggggtggagagcaactccgatgggcctccccggagccctgcaccgt
caccctggtgccgtgaagctggaaggagaagctggagcaaaacccgg
aggagtcccaggacatcaaagctctgcagaaagaactcgagcaatttgcc
aagctcctgaagcagaagaggatcaccctgggatatacacaggccgatgt
ggggctcaccctgggggttctatttgggaaggtattcagccaaacgacca
tctgccgctttgaggctctgcagcttagcttcaagaacatgtgtaagctg
cggcccttgctgcagaagtgggtggaggaagctgacaacaatgaaaatct
tcaggagatatgcaaagcagaaaccctcgtgcaggcccgaaagagaaagc
gaaccagtatcgagaaccgagtgagaggcaacctggagaatttgttcctg
cagtgccccgaaaccccaactgcagcagatcagccacatcgcccagcagct
tgggctcgagaaggatggtccgagtgtggttctgtaaccggcgccaga
agggcaagcgatcaagcagcgactatgcacaacgagaggattttgaggct
gctgggtctcctttctcaggggggaccagtgtcctttcctctggccccagg
gccccattttggtacccaggctatgggagccctcacttcactgactgt
actcctcggtcccctttccctgaggggggaagcctttccccctgtctctgtc
accactctgggctctcccatgcattcaaactga
```
describes Human OCT4 nucleotide sequence.

(SEQ ID NO: 21)
MAGHLASDFAFSPPPGGGGDGPGGPEPGWVDPRTWLSFQGPPGGPGIGPG
VGPGSEVWGIPPCPPPYEFCGGMAYCGPQVGVGLVPQGGLETSQPEGEAG
VGVESNSDGASPEPCTVTPGAVKLEKEKLEQNPEESQDIKALQKELEQFA
KLLKQKRITLGYTQADVGLTLGVLFGKVFSQTTICRFEALQLSFKNMCKL
RPLLQKWVEEADNNENLQEICKAETLVQARKRKRTSIENRVRGNLENLFL
QCPKPTLQQISHIAQQLGLEKDVVRVWFCNRRQKGKRSSSDYAQREDFEA
AGSPFSGGPVSFPLAPGPHFGTPGYGSPHFTALYSSVPFPEGEAFPPVSV
TTLGSPMHSN
describes Human OCT4 amino acid sequence.

(SEQ ID NO: 22)
```
atggccaacctggagcgcaccttcatcgccatcaagccggacggcgtgca
gcgcggcctggtgggcgagatcatcaagcgcttcgagcagaaggggattcc
gcctcgtggccatgaagttcctccgggcctctgaagaacacctgaagcag
cactacattgacctgaaagaccgaccattcttccctgggctggtgaagta
catgaactcagggcgcttggtggccatgtggaggggctgaacgtgg
tgaagacaggccgagtgatgctggggagaccaatccagcagattcaaag
ccaggcaccattcgtggggacttctgcattcaggttggcaggaacatcat
tcatggcagtgattcagtaaaaagtgctgaaaaagaaatcagcctatggt
ttaagctcgaagaactggttgactacaagtcttgtgctcatgactgggtc
tatgaataa
```
describes NM23-H2 nucleotide sequence (NM23-H2:
GENBANK ACCESSION AK313448).

(SEQ ID NO: 23)
MANLERTFIAIKPDGVQRGLVGEIIKRFEQKGFRLVAMKFLRASEEHLKQ
HYIDLKDRPFFPGLVKYMNSGPVVAMVWEGLNVVKTGRVMLGETNPADSK
PGTIRGDFCIQVGRNIIHGSDSVKSAEKEISLWFKPEELVDYKSCAHDWV
YE
describes NM23-H2 amino acid sequence (NM23-H2:
GENBANK ACCESSION AK313448).

(SEQ ID NO: 24)
```
atggctgtcagcgacgcgctgctcccatctttctccacgttcgcgtctgg
cccggcgggaagggagaagacactgcgtcaagcaggtgccccgaataacc
gctggcgggaggagctctcccacatgaagcgacttcccccagtgcttccc
gccggccctatgcctggcggcggcgaccgtggccacagacctggacag
cgccggagccggctgcggcttgcggcggtagcaactcggcgccctacctc
ggagagagaccgaggagtcaacgatctcctggacctggactttattctc
tccaattcgctgacccatcctccggagtcagtggccgccaccgtgtcctc
gtcagctcagcctcctcttcgtcgtccgtcgagcaggcgcctgcca
gcgcccctccacctgcagcttcacctatccgatccgggccggaacgac
ccgggcgtggccgggcggcacgggcggaggcctcctctatgcagggga
gtccgctccccctccgacggctccccttcaacctggcggacatcaacgacg
tgaccctcgggcggctcagttggccgagctcctgccggccagaattggac
ccggtgtacattccgccgccagcgccagccccaggtgggggctgat
gggcaagttcgtgctgaaggcgctcgctgagcgccctggcagcgagtacg
gcagcccgtcggtcatcagcgtcacgaaaggcagccctgacggcagccac
ccggtggtggtgccccctacaacggcgccgcccgacacgtgcccaa
gatcaagcaggaggcggtctcttcgtgcaccccactgggcgctggaccca
ctctcagcaatggccaccggccggctgcacacgacttcccctggggcgg
cagctcccagcaggactaccccgaccctgggtcttgaggaagtgctgag
cagcagggactgtcaccctgccctgccgcttcctcccggcttccatccc
acccggggcccaattacccatccttcctgcccgatcagatgcagccgaa
gtcccgccgctccattaccaagagctcatgccaccgggttcctgcatgcc
agaggagcccaagccaaagaggggaagacgatcgtggccccggaaaagga
ccgccacccacacttgtgattacgcgggctgcggcaaaacctacacaaag
agttcccatctcaaggcacacctgcgaacccacacaggtgagaaacctta
ccactgtgactgggacggctgtgatggaaattcgcccgctcagatgaac
tgaccaggcactaccgtaaacacacggggcaccgccccgttccagtgccaa
aaatgcgaccgagcattttccaggtcggaccacctcgccttacacatgaa
gaggcatttt
```
describes KLF4 nucleotide sequence (KLF4: GENBANK
ACCESSION AF022184).

(SEQ ID NO: 25)
MAVSDALLPSFSTFASGPAGREKTLRQAGAPNNRWREELSHMKRLPPVLP
AGPYDLAAATVATDLESAGAGAACGGSNLAPLPRRETEEFNDLLDLDFIL
SNSLTHPPESVAATVSSSASASSSSSPSSSGPASAPSTCSFTYPIRAGND
PGVAPGGTGGGLLYGRESAPPPTAPFNLADINDVSPSGGFVAELLRPELD
PVYIPPQQPQPPGGGLMGKFVLKASLSAPGSEYGSPSVISVTKGSPDGSH
PVVVAPYNGGPPRTCPKIKQEAVSSCTHLGAGPPLSNGHRPAAHDFPLGR
QLPSRTTPTLGLEEVLSSRDCHPALPLPPGFHPHPGPNYPSFLPDQMQPQ
VPPLHYQELMPPGSCMPEEPKPKRGRRSWPRKRTATHTCDYAGCGKTYTK
SSHLKAHLRTHTGEKPYHCDWDGCGWKFARSDELTRHYRKHTGHRPFQCQ
KCDRAFSRSDHLALHMKRHF
describes KLF4 amino acid sequence (KLF4: GENBANK
ACCESSION AF022184).

(SEQ ID NO: 26)
```
atggatttttttcgggtagtggaaaaccagcagcctccgcgacgatgcc
cctcaacgttagcttcaccaacaggaactatgacctcgactacgactcgg
tgcagccgtatttctactgcgacgaggaggagaacttctaccagcagcag
cagcaggcgagctgcagcccccggcgcccagcgaggatatctggaagaa
attcgagctgctgccccaccccgccctgtccccatagccgccgctccgggc
tctgctcgccctcctacgttgcggtcacaccctttctcccttcgggggagac
aacgacggcggtggcgggagcttctccacggccgaccagctggagatggt
gaccgagctgctgggaggagacatggtgaaccagagtttcatctgcgacc
cggacgacgagaccttcatcaaaaacatcatccaggactgtatgtgg
agcggcttctcggcctgccgccaagctcgtctcagaagaagctggcctccta
ccaggctgcgcgcaaagacagcggcagcccgaacccgcccgcggccaca
gcgtctgctccacctccagcttgtacctgcaggatctgagcgccgccgcc
tcagagtgcatcgacccctcggtggtcttccctaccctctcaacgacag
cagctcgcccaagtcctgcgcctcgcaagactccagcgccttctctccgt
cctcggattctctgctctcctcgacggagtcctccccgcagggcagccc
gagcccctggtgctccatgaggagacaccgcccaccaccagcagcgactc
tgaggaggaacaagaagatgaggaagaaatcgatgttgtttctcgtgaa
agaggcaggctcctggcaaaaggtcagagtctgcagtcaccttctgctgga
ggccacagcaaacctcctcacagcccactggtcctcaagaggtgccacgt
ctccacacatcagcacaactacgcagcgcctcctccactcggaaggact
atcctgctgccagaggtgcaagttgacagtgtcagagtcctgaggcaca
atcagcaacaaccgaaatgcaccagccccaggtcctcggacaccgagga
gaatgtcaagaggcgaacacacaacgtcttggagcgccagaggaggaacg
agctaaaacggagctttttgccctgcgtgaccagatcccggagttggaa
aacaatgaagaaggccccaaggtagttatccttaaaaaagccacagcata
catcctgtccgtccaagcagaggagcaaaagctcatttctgaagaggact
tgttgcggaaacgacgagaacagttgaaacacaaacttgaacagctacgg
aactcttgtgcg
```
describes c-Myc nucleotide sequence (c-Myc:
GENBANK ACCESSION BC000917).

(SEQ ID NO: 27)
MDFFRVVENQQPPATMPLNVSFTNRNYDLDYDSVQPYFYCDEEENFYQQQ
QQSELQPPAPSEDIWKKFELLPTPPLSPSRRSGLCSPSYVAVTPFSLRGD
NDGGGGSFSTADQLEMVTELLGGDMVNQSFICDPDDETFIKNIIIQDCMW
SGFSAAAKLVSEKLASYQAARKDSGSPNPARGHSVCSTSSLYLQDLSAAA
SECIDPSVVFPYPLNDSSSPKSCASQDSSAFSPSSDSLLSSTESSPQGSP
EPLVLHEETPPTTSSDSEEEQEDEEEIDVVSVEKRQAPGKRSESGSPSAG
GHSKPPHSPLVLKRCHVSTHQHNYAAPPSTRKDYPAAKRVKLDSVRVLRQ
ISNNRKCTSPRSSDTEENVKRRTHNVLERQRRNELKRSFFALRDQIPELE
NNEKAPKVVILKKATAYILSVQAEEQKLISEEDLLRKRREQLKHKLEQLR
NSCA
describes c-Myc amino acid sequence (c-Myc:
GENBANK ACCESSION BC000917).

(SEQ ID NO: 28)
```
atgggctccgtgtccaaccagcagtttcaggtggctgcgccaaggcggc
agaagaggcgcccgaggaggcgccggaggacgcggcccggcggcggacg
agcctcagctgctgcacggtgcgggcatctgtaagtggttcaacgtgcgc
atgggggttcggcttcctgtccatgaccgcccgcgcggggtcgcgctcga
ccccccagtggatgtctttgtgcaccagagtaagctgcacatggaaggt
tccggagctctgaagaggtgaggcagtggagttcaccttttaagaagtca
gccaagggtctggaatccatccgtgtcaccgacctggtggagtattctg
tattgggagtgagaggcggccaaaaggaaagagcatgcagaagcgcagat
caaaaggagacaggtgctacaactgtggaggtctagatcatcatgccaag
```

-continued
gaatgcaagctgccaccccagcccaagaagtgccacttctgccagagcat
cagccatatggtagcctcatgtccgctgaaggcccagcagggccctagtg
cacagggaaagccaacctactttcgagaggaagaagaagaaatccacagc
cctaccctgctcccggaggcacagaat
describes LIN28 nucleotide sequence (LIN28:
GENBANK ACCESSION AF521099).

(SEQ ID NO: 29)
MGSVSNQQFAGGCAKAAEEAPEEAPEDAARAADEPQLLHGAGICKWFNVR
MGFGFLSMTARAGVALDPPVDVFVHQSKLHMEGFRSLKEGEAVEFTFKKS
AKGLESIRVTGPGGVFCIGSERRPKGKSMQKRRSKGDRCYNCGGLDHHAK
ECKLPPQPKKCHFCQSISHMVASCPLKAQQGPSAQGKPTYFREEEEEIHS
PTLLPEAQN
describes LIN28 amino acid sequence (LIN28:
GENBANK ACCESSION AF521099).

(SEQ ID NO: 30)
atgtctcccgcccaagacctcccgttgtctcctgctccccctgctcac
gctcggcaccgcgctcgcctcctcggctcggcccaaagcagcagcttca
gccccgaagcctggctacagcaatatggctacctgcctcccggggaccta
cgtacccacacacagcgctcaccccagtcactctcagcggccatcgctgc
catgcagaagttttacggcttgcaagtaacaggcaaagctgatgcagaca
ccataaaggccatgaggcgccccgatgtggtgttccagacaagtttggg
gctgagatcaaggccaatgttcgaaggaagcgctacgccatccagggtct
caaatggcaacataatgaaatcactttctgcatccagaattacacccca
aggtgggcgagtatgccacatacgaggccattcgcaaggcgttccgcgtg
tgggagagtgccacaccactgcgcttccgcgaggtgccctatgcctacat
ccgtgaggccatgaagcaggccgacatcatgatcttcttgccgagg
gcttccatggcgacagcacgcccttcgatggtgagggcggcttcctggcc
catgcctacttcccaggccccaacattggaggagacacccactttgactc
tgccgagccttggactgtcaggaatgaggatctgaatggaaatgacatct
tcctggtggctgtgcacgagctgggccatgccctggggctcgagcattcc
agtgacccctcggccatcatggcaccctttaccagtggatggacacgga
gaattttgtgctgcccgatgatgaccgccggggcatccagcaactttatg
ggggtgagtcagggttccccaccaagatgccccctcaacccaggactacc
tcccggccttctgttcctgataaaccccaaaaacccccacctatgggcccaa
catctgtgacgggaactttgacaccgtggccatgctccgaggggagatgt
ttgtcttcaaggagcgctggttctggcgggtgaggaataaccaagtgatg
gatggataccaaatgcccattggccagttctggcggggcctgcctgcgtc
catcaacactgcctacgagaggaaggatggcaaattcgtcttcttcaaag
gagacaagcattgggtgtttgatgaggcgtccctggaaccttggctacccc
aagcacattaaggagctgggccgagggctgcctaccgacaagattgatgc
tgctctcttctggatgcccaatggaaagaccctacttcttccgtggaaaca
agtactaccgtttcaacgaagagctcagggcagtggatagcgagtacccc
aagaacatcaaagtctgggaagggatccctgagtctcccagagggtcatt
catgggcagcgatgaagtcttcacttacttctacaaggggaacaaatact
ggaaattcaacaaccagaagctgaaggtagaaccgggctaccccaagtca
gccctgagggactggatgggctgcccatcgggaggccggccggatgaggg
gactgaggaggagacggaggtgatcatcattgaggtggacgaggagggcg
gcggggcggtgagcgcggctgccgtggtgctgcccgtgctgctgctgctc
ctggtgctggcggtgggccttgcagtcttcttcagacgccatgggac
ccccaggcgactgctctactgccagcgttccctgctggacaaggtc
describes MMP14 nucleotide sequence (MMP14:
GENBANK ACCESSION BC064803).

(SEQ ID NO: 31)
MSPAPRPSRCLLLPLLTLGTALASLGSAQSSSFSPEAWLQQYGYLPPGDL
RTHTQRSPQSLSAAIAAMQKFYGLQVTGKADADTMKAMRRPRCGVPDKFG
AEIKANVRRKRYAIQGLKWQHNEITFCIQNYTPKVGEYATYEAIRKAFRV
WESATPLRFREVPYAYIREGHEKQADIMIFFAEGFHGDSTPFDGEGGFLA
HAYFPGPNIGGDTHFDSAEPWTVRNEDLNGNDIFLVAVHELGHALGLEHS
SDPSAIMAPFYQWMDTENFVLPDDDRRGIQQLYGGESGFPTKMPPQPRTT
SRPSVPDKPKNPTYGPNICDGNFDTVAMLRGEMFVFKERWFWRVRNNQVM
DGYPMPIGQFWRGLPASINTAYERKDGKFVFFKGDKHWVFDEASLEPGYP
KHIKELGRGLPTDKIDAALFWMPNGKTYFFRGNKYYRFNEELRAVDSEYP
KNIKVWEGIPESPRGSFMGSDEVFTYFYKGNKYWKFNNQKLKVEPGYPKS
ALRDWMGCPSGGRPDEGTEEETEVIIIEVDEEGGGAVSAAAVVLPVLLLL
LVLAVGLAVFFFRRHGTPRRLLYCQRSLLDKV
describes MMP14 amino acid sequence (MMP14:
GENBANK ACCESSION BC064803).

(SEQ ID NO: 32)
atgatcttactcacattcagcactggaagacggttggatttcgtgcatca
ttcggggtgttttcttgcaaaccttgctttggattttatgtgctacag
tctgcggaacggagcagtatttcaatgtggaggtttggttacaaaagtac
ggctaccttccaccgactgaccccagaatgtcagtgctgcgctctgcaga
gaccatgcagtctgccctagctgccatgcagcagttctatggcattaaca
tgacaggaaaagtgacagaaacacaattgactggatgaagaagcccga
tgcggtgtacctgaccagacaagaggtagctccaaatttcatattcgtcg
aaagcgatatgcattgacaggacagaaatggcagcacaagcacatcactt
acagtataaagaacgtaactccaaaagtaggagaccctgagactcgtaaa -continued
gctattcgccgtgcctttgatgtgtggcagaatgtaactcctctgacatt
tgaagaagttccctacagtgaattagaaaatggcaaacgtgatgtggata
taaccattatttttgcatctggtttccatggggacagctctcccctttgat
ggagagggaggattttggcacatgcctacttccctggaccaggaattgg
aggagataccattttgactcagatgagccatggacactaggaaatccta
atcatgatggaaatgactatttcttgtagcagtccatgaactgggacat
gctctgggattggagcattccaatgaccccactgccatcatggctccatt
ttaccagtacatggaaacagacaacttcaaactacctaatgatgatttac
agggcatccagaaaatatatggtccacctgacaagattcctccacctaca
agacctctaccgacagtgcccccacaccgctctattcctccggctgaccc
aaggaaaaatgacaggccaaaacctcctcggcctccaaccggcagaccct
cctatcccggagccaaacccaacatctgtgatgggaactttaacactcta
gctattcttcgtcgtgagatgtttgttttcaaggaccagtggttttggcg
agtgagaaacaacagggtgatggatggataccaatgcaaattacttact
tctggcggggcttgcctcctagtatcgatgcagtttatgaaaatagcgac
gggaattttgtgttcttcaaaggtaacaaatattgggtgttcaaggatac
aactcttcaacctggttaccctcatgacttgataaccctggaagtggaa
ttccccctcatggtattgattcagccatttggtgggaggacgtcgggaaa
acctattctcttcaaggagacagatattggagatatagtgaagaaatgaa
aacaatggaccctggctatcccaagccaatcacagtctggaaagggatcc
ctgaatctcctcagggagcatttgtacacaaagaaaatggctttacgtat
ttctacaaaggaaagagtattggaaattcaacaaccagatactcaaggt
agaacctggacatccaagatccatcctcaaggattttatgggctgtgatg
gaccaacagacagagttaaagaaggacacagcccaccagatgatgtagac
attgtcatcaaactggacaacacagccagcactgtgaaagccatagctat
tgtcattccctgcatcttggccttatgcctccttgtattggtttacactg
tgttccagttcaagaggaaaggaacaccccgccacatactgtactgtaaa
cgctctatgcaagagtgggtg
describes MMP16 nucleotide sequence (MMP16:
GENBANK ACCESSION AB009303).

(SEQ ID NO: 33)
MILLTFSTGRRLDFVHHSGVFFLQTLLWILCATVCGTEQYFNVEVWLQKY
GYLPPTDPRMSVLRSAETMQSALAAMQQFYGINMTGKVDRNTIDWMKKPR
CGVPDQTRGSSKFHIRRKRYALTGQKWQHKHITYSIKNVTPKVGDPETRK
AIRRAFDVWQNVTPLTFEEVPYSELENGKRDVDITIIFASGFHGDSSPFD
GEGGFLAHAYFPGPGIGGDTHFDSDEPWTLGNPNHDGNDLFLVAVHELGH
ALGLEHSNDPTAIMAPFYQYMETDNFKLPNDDLQGIQKIYGPPDKIPPPT
RPLPTVPPHRSIPPADPRKNDRPKPPRPPTGRPSYPGAKPNICDGNFNTL
AILRREMFVFKDQWFWRVRNNRVMDGYPMQITYFWRGLPPSIDAVYENSD
GNFVFFKGNKYWVFKDTTLQPGYPHDLITLGSGIPPHGIDSAIWWEDVGK
TYFFKGDRYWRYSEEMKTMDPGYPKPITVWKGIPESPQGAFVHKENGFTY
FYKGKEYWKFNNQILKVEPGHPRSILKDFMGCDGPTDRVKEGHSPPDDVD
IVIKLDNTASTVKAIAIVIPCILALCLLVLVYTVFQFKRKGTPRHILYCK
RSMQEWV
describes MMP 16 amino acid sequence (MMP16:
GENBANK ACCESSION AB009303)

Induction of Pluripotency

It was recently discovered that somatic cells can be reprogrammed to revert to the pluripotent state. The genes that code for transcription factors OCT4, SOX2, KLF4, NANOG, c-MYC and LIN28 or the proteins themselves can be introduced into somatic cells and cause a reversion to the pluripotent state. Many of these pluripotency factors were previously thought of as oncogenes. C-Myc is a well known oncogene and similarly, Klf4 has been shown to induce dysplasia (Foster et al., 2005). OCT4 was identified as the gold standard for identifying pluripotent stem cells. The presence of OCT4 in the nucleus indicates that the cell is pluripotent and its absence indicates that the cell has entered the differentiation process and is no longer able to differentiate into any cell type. Recently, it became known that OCT4 is also present in the nucleus of many cancer cells, but not in normal mature cells. The present inventors recently discovered that a cleaved form of the MUC1 transmembrane protein (SEQ ID NO:1), MUC1*, is a powerful growth factor receptor that is expressed on an estimated 75% of solid tumor cancers (Raina et al., 2009) and that it is also expressed in this "tumorigenic" form on pluripotent stem cells (Hikita et al., 2008). The present invention relates to MUC1* and MUC1* associated factors as well as methods employing them for the induction or maintenance of pluripotency or to enhance the efficiency of inducing pluripotency.

The present invention encompasses using MUC1* associated factors, which include protein factors, genes that encode them, or small molecules that affect their expression, to induce or improve the efficiency of generating iPS cells. We have shown that a cleaved form of the MUC1 transmembrane protein—MUC1*—is a primal growth factor receptor that mediates the growth of both cancer and pluripotent stem cells. Interrupting the interaction between MUC1* extracellular domain and its activating ligand, NM23, is lethal to pluripotent stem cells (Hikita et al., 2008) which indicates that this pathway is critical for pluripotency. NM23 is a ligand that activates MUC1* (Mahanta et al., 2008) (SEQ ID NOS:12-17 and 22-23). In addition to its ability to stimulate pluripotent stem cell growth, while inhibiting differentiation, NM23 has been shown to induce transcription of c-Myc (Dexheimer at al., 2009). Therefore, adding NM23 to cells undergoing conversion to the pluripotent state will provide the benefits of transfecting the c-Myc oncogene, while mitigating the associated health risks. In addition, stimulation of MUC1*, by either NM23 or a bivalent anti-MUC1* antibody, activates the MAP kinase proliferation pathway, which increases cell survival (Mahanta et al., 2008). NANOG expression induces pluripotency; the tumor suppressor p53 suppresses Nanog expression (Lin et al., 2007). Therefore, the need for NANOG for inducing pluripotency is reduced or eliminated by suppressing p53. An ectopically expressed 72-amino acid fragment of the MUC1 cytoplasmic tail (MUC10-CT) has been shown to be present in the nucleus of cancer cells where it binds to the p53 promoter (Wei et al., 2007). The approximately 72 amino acid fragment of MUC1-CD such as shown in SEQ ID NO:11 can be used in combination with other pluripotency-inducing factors to induce or enhance iPS cell generation. However, this peptide does not correspond to a naturally occurring MUC1 species, and therefore may produce undesired effects. The present inventors disclose that MUC1* translocates to the nucleus (Examples 1 and 9, and FIG. 6) and therefore is used alone or in combination with other pluripotency-inducing factors to induce or enhance iPS cell generation. In support of this approach, it has been reported that several genes from the core set of pluripotency genes regulate transcription of MUC1, its cleavage enzyme and/or its activating ligand NM23 (Boyer et al., 2005). OCT4 and SOX2 bind to the MUC1 promoter and also to the promoter of its cleavage enzyme, MMP-14. SOX2 and NANOG bind to the NM23 promoter. Given that MUC1* is critical for maintenance of hESCs and is the target of the key pluripotency genes, we disclose that the introduction of MUC1*, or agents that increase cleavage of MUC1 to the MUC1* form, along with its activating ligand, NM23 can be used to replace some or all of the previously identified pluripotency-inducing factors to induce or enhance the generation of iPS cells.

The present invention discloses novel reagents and methods, involving MUC1*, for inducing pluripotency in cells. These reagents and methods are used to induce pluripotency in somatic or mature cells. In another aspect of the invention, they are used to increase the efficiency of inducing pluripotency in mature cells. In yet another aspect of the invention they are used to maintain immature cells in an immature state. In another aspect of the invention they are used to inhibit differentiation. In another aspect of the invention, these reagents and methods are used for maintaining stem cells in the pluripotent state.

The invention involves reversing differentiation or maintaining stem-like characteristics by introducing to mature cells, or somewhat differentiated cells, genes or gene products that affect the expression of MUC1* and its associated factors. MUC1* is the cleaved form of the transmembrane protein MUC1. MUC1* associated factors include, but are not limited to, full-length MUC1, enzymes that cleave MUC1, MUC1* activating ligands and also transcription factors that affect the expression of MUC1 or MUC1*. The invention is also drawn to the introduction of the genes or gene products for MUC1* or MUC1* associated factors to mature cells or somewhat differentiated cells will induce pluripotency or stem-ness in those cells or their progeny. The present application describes their use for maintaining pluripotency in stem cells. Agents that affect expression of MUC1* or MUC1* associated factors can be added in combination with, or to replace one or more genes or gene products that are already known to induce pluripotency including OCT4, SOX2, KLF4, NANOG, c-myc and LIN28.

Forced expression of combinations of the transcription factors, Oct4, Sox2, Klf4 and c-Myc or Oct4, Sox2, Nanog and Lin28 have been shown to cause mature cells to revert to the pluripotent state (Takahashi and Yamanaka, 2006). Each of the transcription factors that induce pluripotency regulates the transcription of about a dozen genes. Among these were several that the inventor has identified as being MUC1-associated factors. OCT4 and SOX2 bind to the MUC1 promoter itself. SOX2 and NANOG bind to the NM23 (NME7) promoter. NM23 (also known as NME) was previously identified, by the present inventor, as the activating ligand of MUC1* (Mahanta et al., 2008). NME7 is an activating ligand of MUC1*. OCT4 and SOX2 both bind to the promoter for MMP16 which we disclose herein is a cleavage enzyme of MUC1. OCT4, SOX2 or NANOG also bind to promoter sites for cleavage enzymes MMP2, MMP9, MMP10, ADAM TSL-1, ADAM TS-4, ADAM-17 (a MUC1 cleavage enzyme), ADAM-TS16, ADAM-19 and ADAM-28. Some or all of these cleavage enzyme may be upregulated to enhance the cleavage of MUC1 to the MUC1* form to induce pluripotency or maintain it (Boyer et al, 2005).

Our previous work with embryonic stem cells, which only express the cleaved form of MUC1, MUC1*, showed that dimerization of its extracellular domain stimulate growth and inhibit differentiation (Hikita et al., 2008). These effects were achieved by dimerizing the MUC1* extracellular domain using either a bivalent Anti-MUC1* antibody, recombinant NM23, or a mutant NM23 (S120G) that preferentially forms dimers (Kim et al., 2003). Inhibition of MUC1* extracellular domain using the monovalent Anti-MUC1* Fab was lethal within hours. These findings indicate that MUC1* is a significant "stemness" factor. In addition, OCT4 and SOX2 bind to the MUC1 gene promoter and also to the promoter of its cleavage enzymes. SOX2 and NANOG bind to the NM23 (NME7) promoter. Since blocking the extracellular domain of MUC1* are lethal to hESCs, it follows that the pluripotency genes, OCT4, SOX2, and NANOG, are induce expression of MUC1, its cleavage enzyme and its activating ligand. One or more of the genes or gene products that have already been shown to induce pluripotency can be replaced by transfecting the gene or introducing the gene product, for MUC1* alone or in addition to its cleavage enzymes and/or activating ligands, NME7, NME-H1, NME-H2 or an antibody that dimerizes the PSMGFR epitope of MUC1 or MUC1*.

As those who are skilled in the art are familiar, signal sequences that direct the localization of the transfected gene product may be added to the gene. Examples of signal sequences are given as SEQ ID NOS:2-4. The invention contemplates that the N-terminal domain of MUC1* may be truncated or extended by up to nine (9) amino acids without substantially altering the effect of these genes or gene products. MUC1* exemplified as SEQ ID NO:5 and variants whose extracellular domain is essentially comprised of the sequences given in SEQ ID NOS: 6, 7, 8 and 9 are preferred.

MUC1, MUC1*, or associated factors, including those listed above, can substitute for one or more of the genes or gene products that induce pluripotency and are used to induce pluripotency or to maintain it.

In one case, somatic cells such as fibroblasts and dermal fibroblasts are transfected with a gene that encodes the MUC1 protein, which aids in inducing stem cell-like features and in some cases induces progeny to become pluripotent stem cells. In another aspect of the invention, a gene for MUC1* is transfected into cells to induce a return to a stem cell-like state and in some cases induce actual pluripotent stem cells. Each of the MUC1 or MUC1* genes may be introduced to the cell alone or in combination with other genes that aid in inducing pluripotency or stem cell-like characteristics. For example, DNA encoding MUC1 or preferentially MUC1* is introduced to the cell along with one or more of the genes that encode OCT4, SOX2, NANOG, LIN28, KLF4, and/or c-Myc. DNA encoding a truncated form of MUC1, preferentially MUC1*, is transfected into fibroblasts along with genes encoding OCT4, SOX2, NANOG, and LIN28 (Yu et al., 2007). In another embodiment, DNA encoding a truncated form of MUC1, preferentially MUC1*, is transfected into somatic cells, fibroblasts, or other cells, along with genes encoding OCT4, SOX2, KLF4, and c-Myc (Takahashi et al., 2007). Similarly, DNA encoding MUC1* and/or its activating ligand, NM23 or the S120G mutant of NM23, are transfected into cells to induce pluripotency. MUC1* and/or NM23 may be transfected along with other genes such as OCT4, SOX2, NANOG, LIN28, KLF4, and/or c-Myc to induce pluripotency or stem cell-like characteristics. DNA encoding antibodies that recognize MUC1* or MUC1 may also be transfected into cells alone or with other genes to induce stem cell characteristics in the cells or their progeny. If secreted, anti-MUC1* antibodies will dimerize and thus activate the MUC1* receptor and its functions that promote or maintain stem-like characteristics.

Similarly, factors such as nucleic acids, proteins, modified proteins or small molecules that affect the expression of MUC1, MUC1* or their associated factors are introduced to cells to induce characteristics of stem cells or to induce a return to pluripotency. For example, genes or gene products for MUC1 cleavage enzymes, MMP14, MMp16, MMP2, MMP9, MMP10, ADAM TSL-1, ADAM TS-4 ADAM-17 (a MUC1 cleavage enzyme), ADAM-TS16, ADAM-19 and ADAM-28 are introduced to cells to induce pluripotency or similar characteristics.

In another embodiment, non-protein agents are added to cells to induce or enhance the induction of pluripotency. For example the phorbol ester phorbol 12-myristate 13-acetate (PMA) is a small molecule that increases the cleavage of MUC1 to MUC1* (Thathiah et al., 2003). In one aspect of the invention, phorbol ester is added to cells undergoing conversion to pluripotency to induce or increase the efficiency of iPS generation.

In another example, ligands that interact with MUC1 or MUC1* are added to somatic cells, dermal fibroblasts, fibroblasts, or somewhat differentiated cells to induce pluripotency either alone or in combination with other genes to induce or maintain pluripotency. For example, one or more of the genes encoding OCT4, SOX2, NANOG, LIN28, KLF4, and/or c-Myc are transfected into fibroblasts or other cells and then are cultured in the presence of ligands that activate MUC1 or MUC1*. Dimeric, protein ligands of MUC1* are preferred. In a preferred embodiment, a bivalent anti-MUC1* antibody is added to cells that have been transfected with genes that influence cells or their progeny to become pluripotent stem cells.

In a preferred embodiment, NM23 (NM23-H1, NM23-H2, or NME7) is introduced to cells, as the gene that encodes it, as the protein itself or as a protein bearing a leader sequence such as a poly-arginine tract, to facilitate entry into the cell, to aid in the induction or maintenance of pluripotency. The inventors recently showed that when NM23 is secreted by pluripotent stem cells (and cancer cells), it is an activating ligand of the cleaved form of MUC1—MUC1*—and triggers the MAP kinase proliferation pathway. NM23 stimulation of MUC1* was shown to promote the growth of pluripotent hESCs and inhibited their differentiation (Hikita et al., 2008). NM23 also induces the transcription of c-MYC (Dexheimer at al., 2009) and replaces the need for c-MYC. NM23 is added exogenously either in its native state to activate the MUC1* growth factor receptor or with a poly arginine tract to facilitate entry into the cell and nucleus where it induces C-MYC expression. NM23 (NME) may be added as the encoding nucleic acid, or as the expressed protein with or without a modification that facilitates entry into the cell. NME-H1, -H2 or -7 can be used in their native state or in mutant forms that favor the dimeric state, such as the S120G mutation.

In another aspect of the invention, a bivalent antibody that binds to the extracellular domain of MUC1* (PSMGFR) or a dimeric MUC1* ligand, such as NM23, or genes encoding them are added to MUC1*-expressing cells to induce pluripotency, increase the efficiency of the induction of pluripotency, to maintain pluripotency or to inhibit differentiation. The cells to which these MUC1 or MUC1* interacting proteins are added may be naturally occurring cells or those into which genes to induce stem cell-like characteristics have been added, or have already entered the differentiation process or may be stem cells.

Genes for inducing pluripotency may be introduced on the same or different plasmids, which may be lenti viral vector driven or adenovirus vectors or any integrating or non-integrating viral or non-viral vector, or any other system that facilitates introduction of these genes into the desired cells.

In many cases, it is preferential to achieve the effects of pluripotency-inducing proteins by introducing the proteins themselves rather than the nucleic acids or genes that encode them. The invention encompasses genes disclosed here for the induction of stem-like characteristics or pluripotency that can be replaced by the gene products, the proteins, either in their native state or modified with leader sequences such as poly-arginine tracts to allow entry into the cells. The products of these genes, i.e. proteins, or other proteins which interact with one or more of the products of the transfected genes are introduced to cells to induce or maintain pluripotency or other stem-cell like characteristics.

In other cases, it may be beneficial to introduce synthetic agents, such as small molecules, to induce stem-ness in mature or differentiated cells (Lyssiotis et al. 2009). In one aspect of the invention, small molecules are added to cells that either directly or indirectly induce the transcription of genes that induce pluripotency. In other cases, small molecules that directly or indirectly increase the production of MUC1* are added. In one instance, these small molecules increase cleavage of MUC1 to the MUC1* form, which is a characteristic of stem cells. Phorbol ester, for example, is a small molecule that increases cleavage of MUC1 to MUC1*, so when added to cells, it promotes induction or maintenance of pluripotent state by generating MUC1*.

P53, which is also known as a tumor suppressor, promotes apoptosis. It would therefore be advantageous to inhibit p53 when culturing stem cells or inducing pluripotency in somatic or other cells. The present invention anticipates using p53 suppressors along with other reagents and methods of the invention to maintain stem-ness or induce stem-like or pluripotent characteristics. P53 can be suppressed by a number of methods. Small molecules such as Pifithrin-μ inhibits the pro-apoptotic effects of p53 (Strom, et al., 2006 September; Komarov, et al., 1999) and thus are optionally added to cells to increase efficiency of induction of pluripotency or to maintain stem-ness. In a preferred embodiment, p53 inhibitors are used along with genes or gene products that up-regulate MUC1 or MUC1*, including but not limited to the MUC1 or MUC1* genes or gene products, their activating ligands and their cleavage enzymes.

Another method for suppressing p53 activity to increase the efficiency of inducing pluripotency or maintaining stem-ness is by the introduction of the MUC1* protein to cell cultures. The MUC1* protein can be modified by adding on a poly-arginine tract to facilitate entry into the cell. It has been reported that the overexpression of the cytoplasmic tail, alone, of MUC1 (MUC1-CD) resulted in its translocation to the nucleus where it was found to bind to the p53 promoter. These studies could not determine whether MUC1-CD down or up-regulated p53. The present invention is also drawn to the repression of p53 by the ectopic expression of MUC1*, to increase the efficiency of inducing pluripotency or other stem-like characteristics. MUC1* can be introduced by inserting the gene into the cell, by adding the protein itself exogenously or by adding the MUC1* protein that is optionally modified with a poly-arginine tract.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1. MUC1* Promotes Growth and Cell Death Resistance

MUC1* promotes clonogenic growth (colony expansion) of fibroblasts. Single cell clones of 3Y1 cells transfected with either full-length MUC1 (SEQ ID NO:1), MUC1*$_{1110}$ (SEQ ID NO:5) or empty vector were plated at 1000 cells per 60 mm dish in DMEM media containing 10% fetal bovine serum, penicillin/streptomycin and G418 (600 μg/ml). Cells were grown for 9 days and then fixed in 4% paraformaldehyde for 15 minutes at room temperature. Dishes were washed with water and then stained with 1% crystal violet in 70% methanol for 20 minutes at room temperature. Dishes were washed three times with water and allowed to dry overnight at room temperature and photographed. FIG. 1A shows that the amount of crystal violet that is absorbed (an indicator of cell number) is much higher where MUC1* single cell clones #3 and #44 are growing. In contrast, cells that transfected with full-length MUC1 (single cell clones #8 and #17) showed no growth rate increase over cells transfected with the empty vector. This shows that the cleaved form, MUC1*, confers a growth and/or survival advantage and not the full-length protein.

Example 2

Figure 1B:
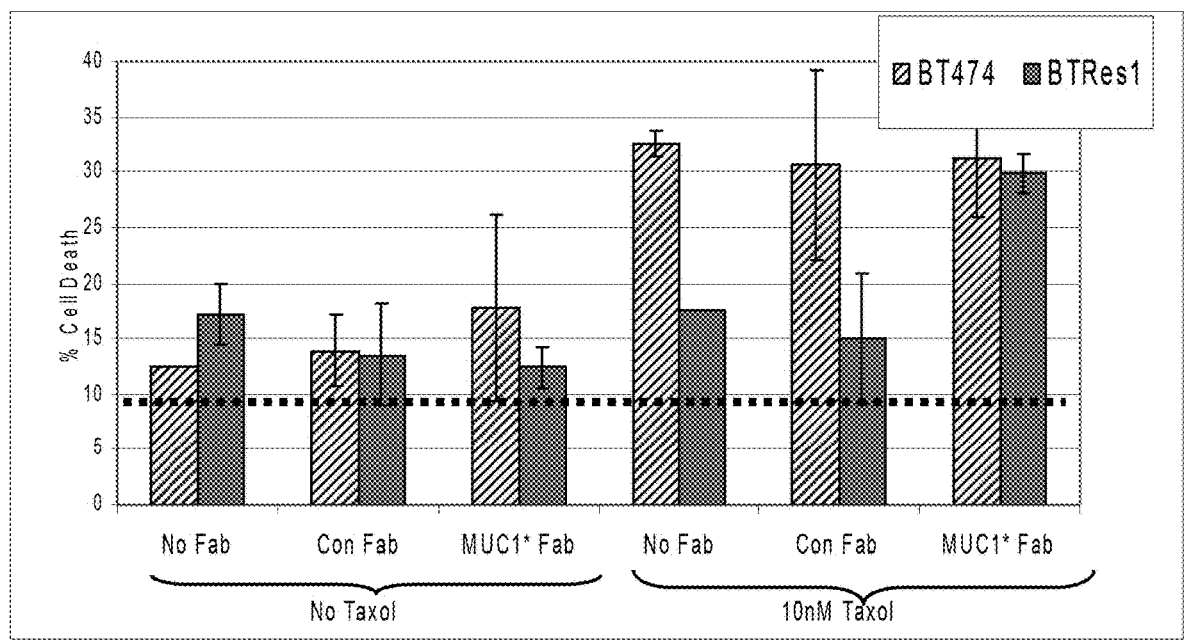

Anti-MUC1* Fab blocks resistance to cell death by Taxol® in trastuzumab (HERCEPTIN®)-resistant cells (made resistant by culture in 1 ug/ml HERCEPTIN®). Fessler et al., 2009 reported that HERCEPTIN® resistant cells are also resistant to TAXOL®, doxorubicin and cyclophosphamide. As reported, these drug resistant cancer cells achieve resistance by overexpressing MUC1*. The following experiment showed that blocking the PSMGFR portion of the MUC1* extracellular domain reversed acquired drug resistance in cancer cells. Parental (BT474) or resistant (BTRes1) cells were plated at a density of 10,000 cells/well in 96 well plates, 4 wells/condition. The following day, Anti-MUC1* Fab, control Fab, or no Fab were added to cells in the presence or absence of TAXOL® (Paclitaxel Sigma T7191). Two days later, cells were resuspended in 50 μl trypsin, and counted in the presence of trypan blue. Percent cell death was calculated as percent trypan blue uptake. BT474 cells underwent cell death in response to TAXOL® under each condition, and BTRes1 cells only underwent cell death in the presence of MUC1* antibody (FIG. 1B).

Example 3

Figure 1C:
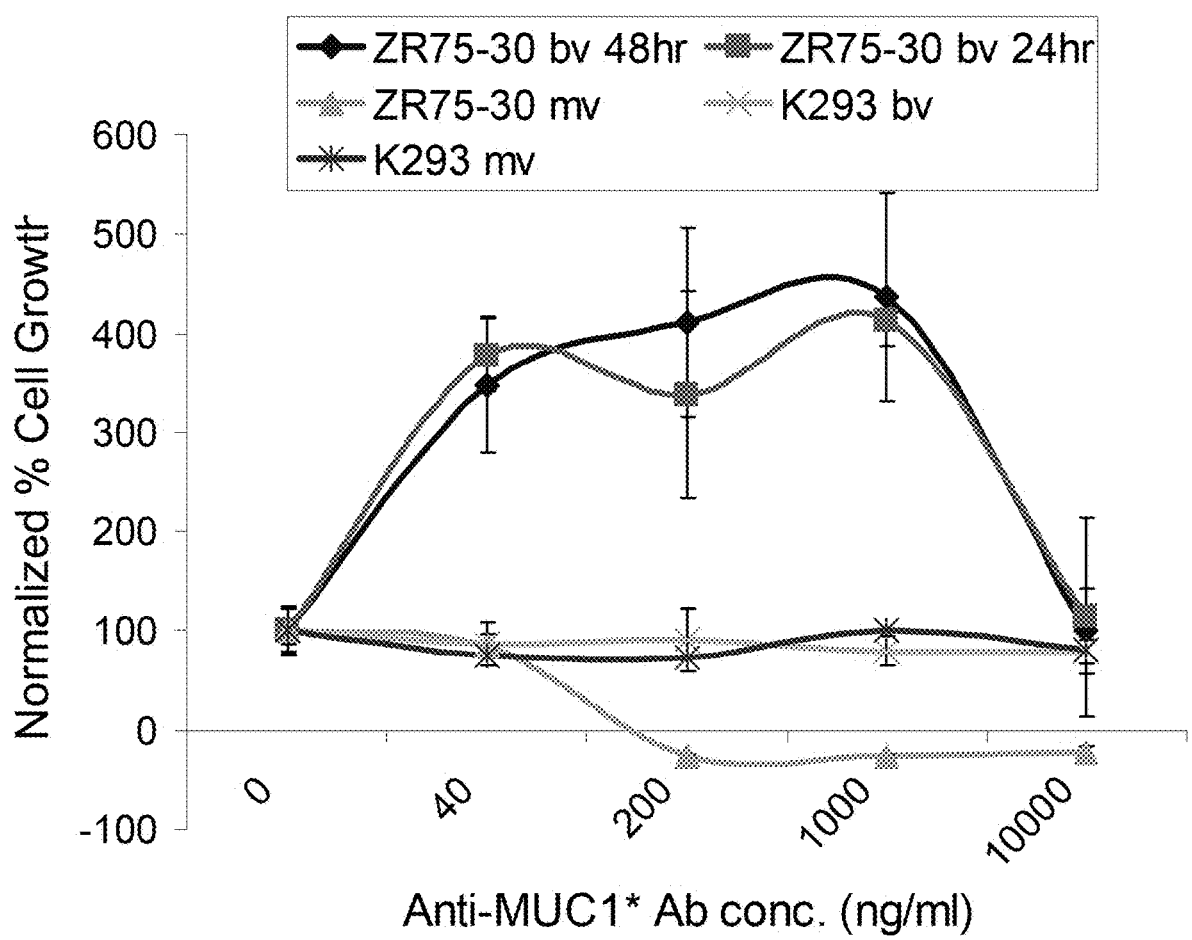
Figure 1D:
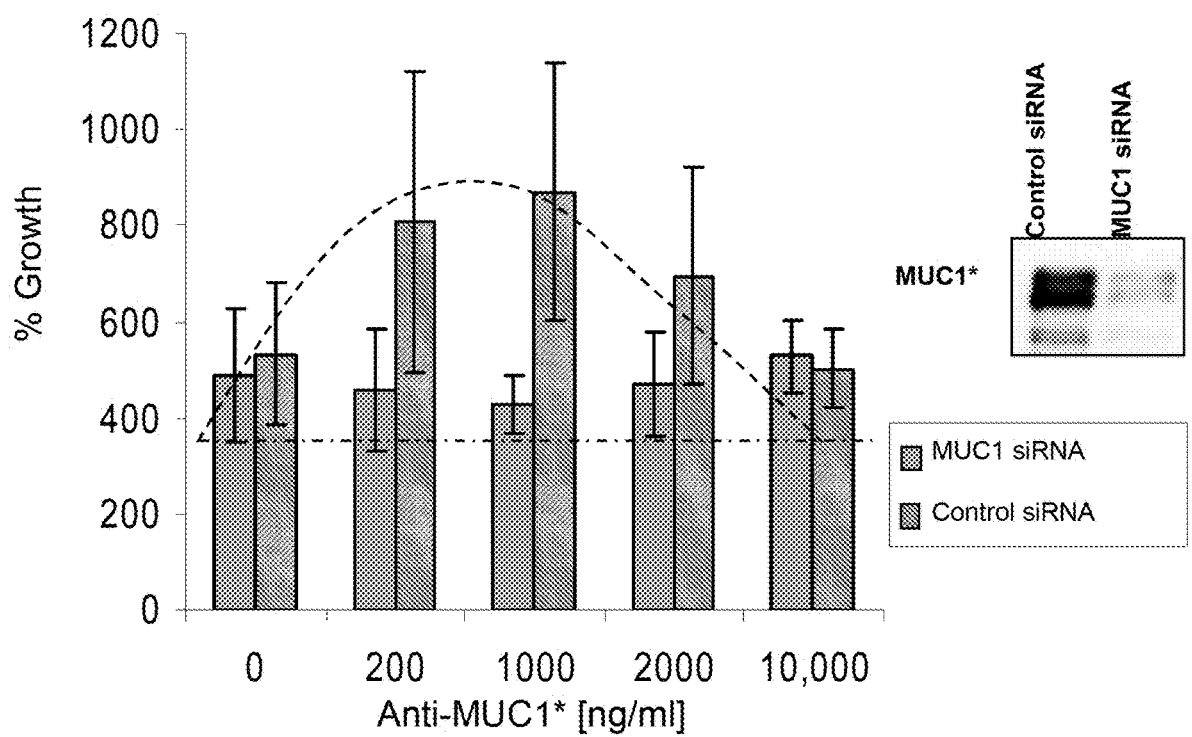
Figure 1E:
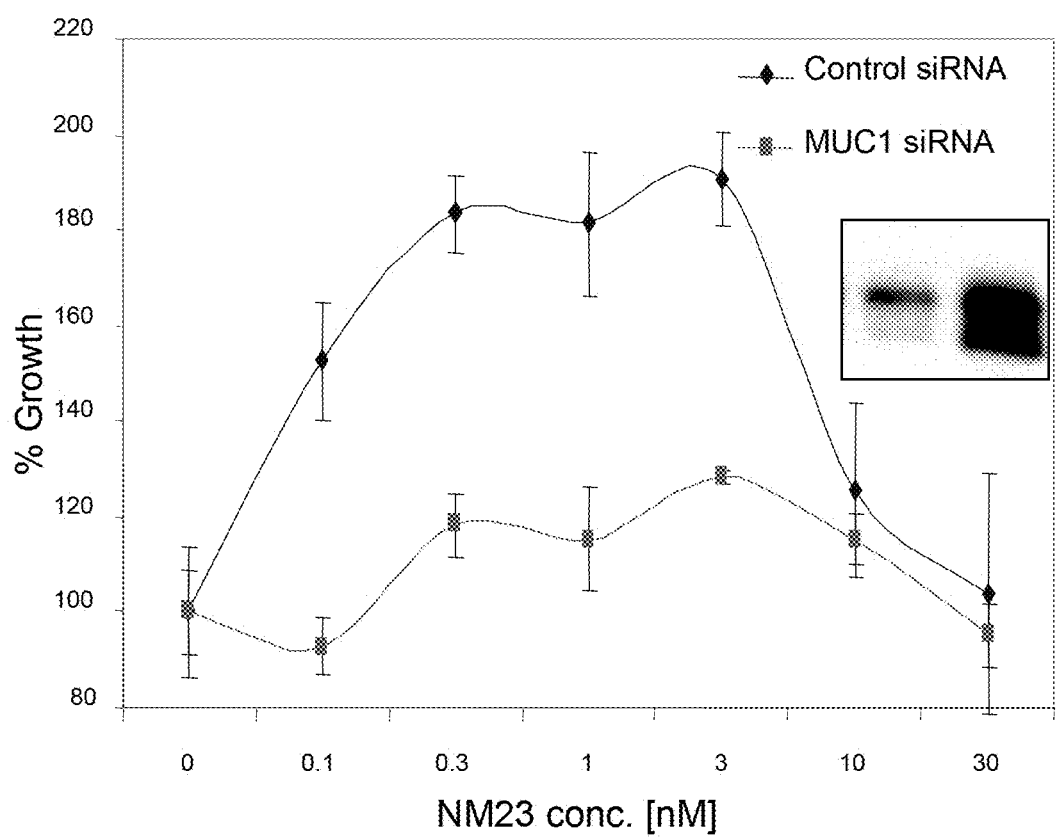

MUC1* acts as a growth factor receptor, and is activated by dimerization of its extracellular domain using an artificial (anti-MUC1* antibody) or its natural ligand, NM23 (NME). MUC1*-positive ZR-75-30 cells, 6000/well, or control (MUC1-negative) HEK293 cells 4000/well, were plated in 96 well plates. The following day, zero hour cell counts were taken, and different concentrations of anti-MUC1* antibody or Fab were added in medium with low (0.1%) serum every 24 or 48 hours. After several days of incubation, cells were resuspended in trypsin and counted, and percent normalized growth was calculated. Stimulation of ZR-75-30 cells, shown as a bell-shaped curve, as is demonstrated for ligand-induced growth stimulation, but not HEK293 cells (FIG. 1C). In a similar experiment, using MUC1*-positive T47D breast cancer cells stably transfected with siRNA targeting MUC1, or control siRNA, stimulation of growth only occurred with control-transfected cells, further demonstrating specificity of antibody (FIG. 1D). Identical results were demonstrated for MUC1*'s natural ligand, NM23 (FIG. 1E).

Example 4

Figure 1F:
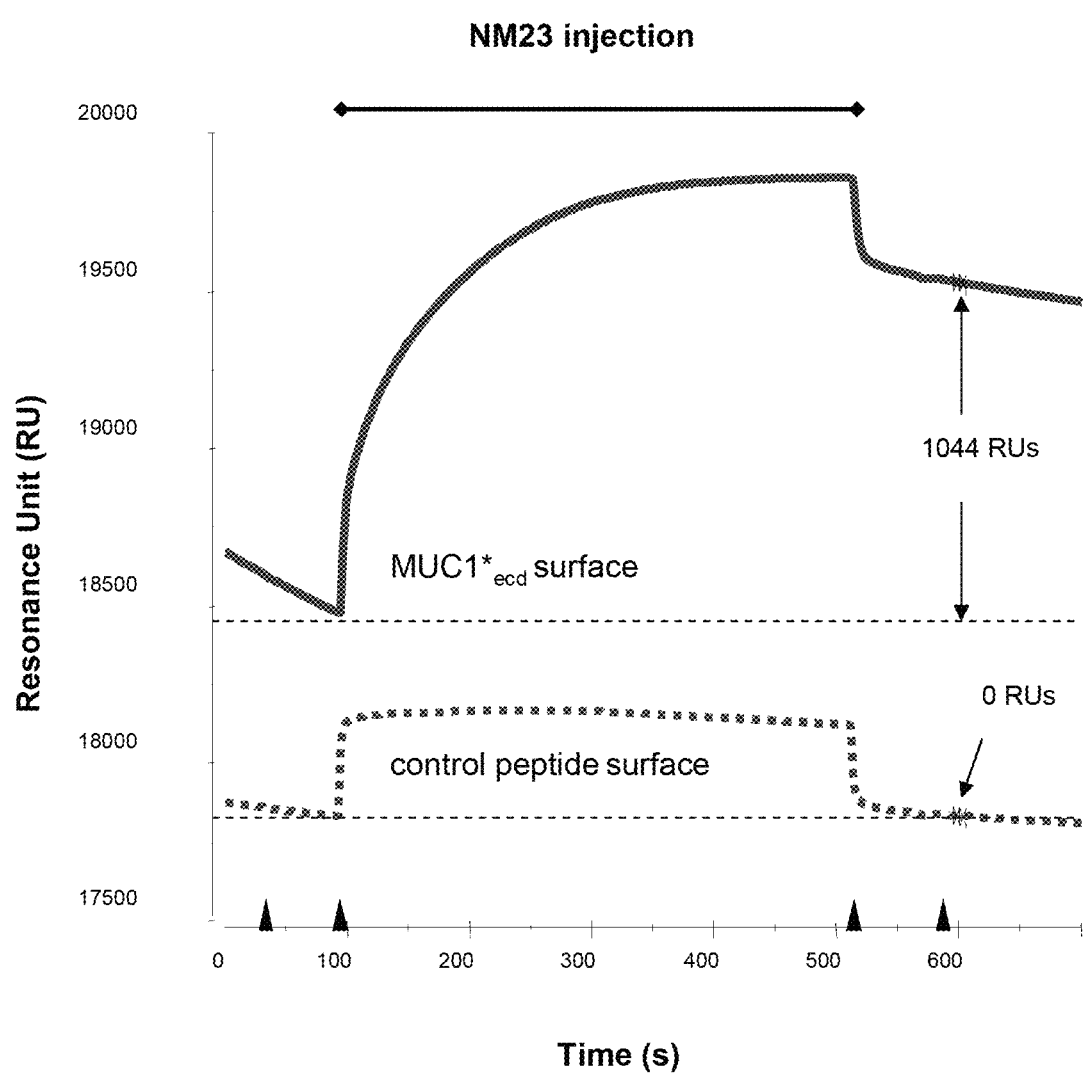

NM23 binds specifically to the PSMGFR peptide which is comprised essentially of the extracellular domain of MUC1*. Binding was measured by Surface Plasmon Resonance, using a Biacore3000 instrument and BiaEvaluation software. Histidine-tagged MUC1*$_{1110-ecd}$ (SEQ ID NO:5) or irrelevant peptide (HHHHHH-SSSSGSSSSGSSSSG-GRGDSGRGDS—SEQ ID NO:34) were immobilized on separate flow channels of 5.7% NTA-Ni$^{++}$ SAM-coated SPR chips, prepared in our lab as described in Mahanta et al. 2008. 35 μL plugs of NM23, purified bovine or recombinant human, were injected into a constant flow stream of 5 uL/minute and sensograms were recorded. NM23 purified from bovine liver (Sigma N-2635) was diluted in PBS alone. Affinities were measured over a wide range of concentrations using a 1:1 Langmuir model. Actual affinities may vary as first order kinetics cannot adequately describe this system. (FIG. 1F).

Example 5

Figure 2:
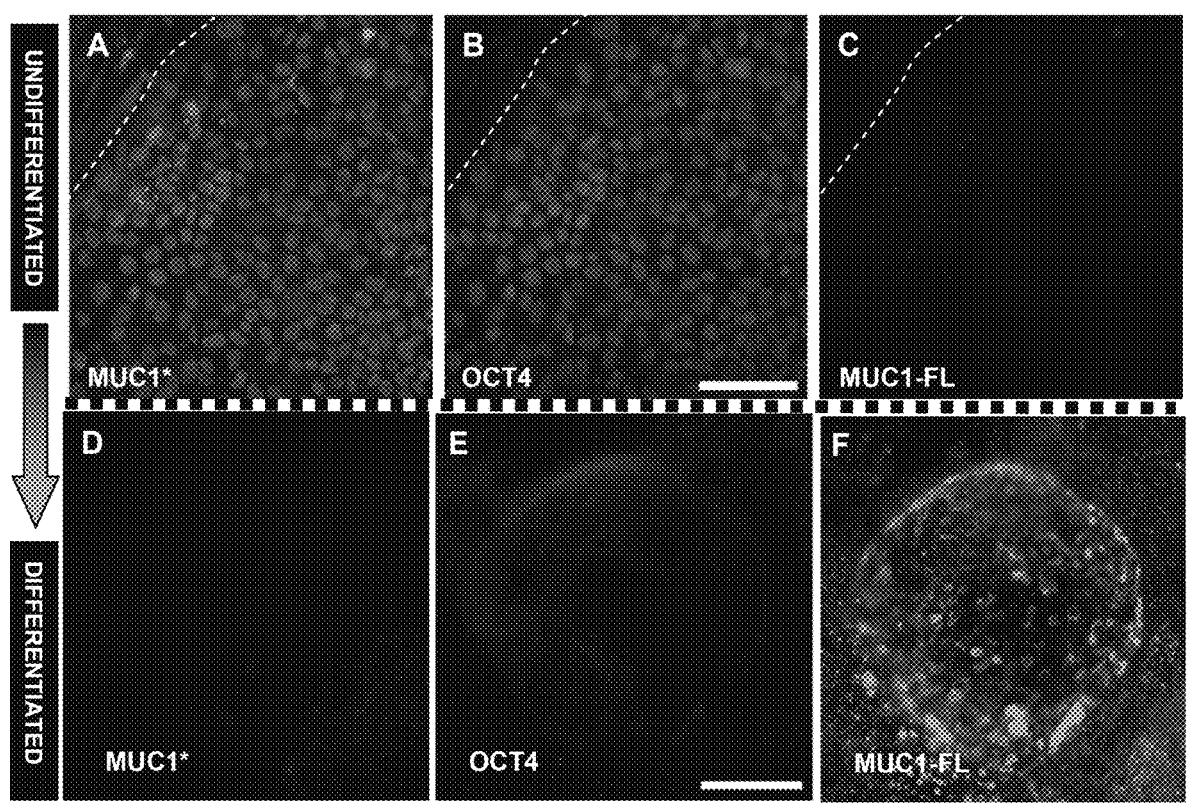
Figure 3:
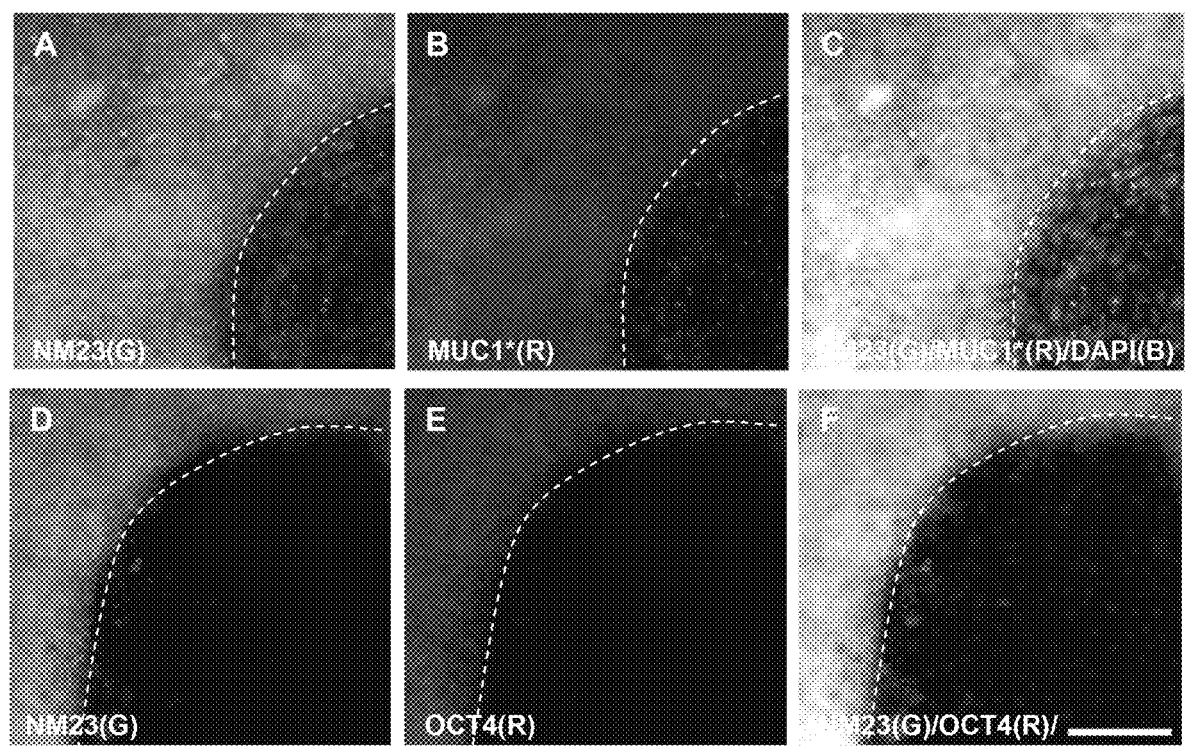

MUC1* Growth Factor Receptor and its ligand NM23 are on undifferentiated hESC, but not differentiated hESC. Human embryonic stem cells in the undifferentiated (pluripotent) state or in the newly differentiating state were analyzed by immunocytochemistry (ICC). Human embryonic stem cells (hESCs) were manually dissected and plated in 8-well chamber slides (NUNC) that had been pre-coated with MATRIGEL. For undifferentiated cells, cells were fixed 5-7 days after plating. For differentiated cells, bFGF was removed from the culture medium 5-7 days after plating and cells were allowed to differentiate for 14 days before fixation. Cells were washed with PBS prior to fixation with 4% paraformaldehyde in 0.1M cacodylate buffer for 15 minutes at 4.degree. C. Cells were blocked for 1 hour with 1% BSA and 1% donkey or goat serum in PBS. 0.1% NP-40 was used with antibodies against intracellular antigens. Primary antibodies were diluted in block and incubated with cells for 1 hour at 4° C. The primary antibodies for the following proteins were used: OCT4 (Santa Cruz, Clone Clones H-134 and C-10, 1:100 dilution), full-length MUC1 (VU4H5, Santa Cruz Biotechnology, 1:50 dilution), MUC1* (Minerva, 1:250 dilution), or NM23 (Santa Cruz, Clone NM301, 1:100 dilution)). Cells were washed 3 times in PBS for 5 minutes prior to incubation for 30 minutes with secondary antibodies: ALEXAFLUOR 488 Goat anti-rabbit IgG, ALEXAFLUOR 555 Goat anti-mouse IgG, ALEXAFLUOR 350 Goat anti-rabbit IgG (Invitrogen, 1:200); Goat anti-mouse IgM-TR (Santa Cruz, 1:100). Cells were washed 3 times in PBS for 5 minutes prior to coverslip mounting using an anti-fade mounting medium (Biomeda). Nuclei were visualized by DAPI staining (1 µg/ml) for 5 minutes. Immunostained cells were visualized on an Olympus BX-51 epifluorescent microscope. Results of these experiments show that MUC1* is on the surface of undifferentiated cells (pluripotent stem cells) (FIGS. 2A, 3B, 3C) but is not on differentiated hESCs (FIG. 2 D). FIG. 3 shows that the ligand of MUC1*, NM23, co-localizes with MUC1* (FIGS. 3A-C). MUC1* and its ligand NM23 are only expressed on pluripotent stem cells (OCT4-positive cells) and not on those that have differentiated, FIGS. 3C and 3F (DAPI stains nuclei of OCT4-negative cells).

Example 6. MUC1* Mediates Growth of Pluripotent Stem Cells

The following experiment was performed to determine the effect of stimulating MUC1*, using a bivalent anti-MUC1*, on pluripotent stem cells. The results show that adding a MUC1* dimerizing ligand stimulates pluripotent (OCT4-positive) stem cell growth and also enables their growth in the absence of feeder cells, their extracts or bFGF.

Figure 4:
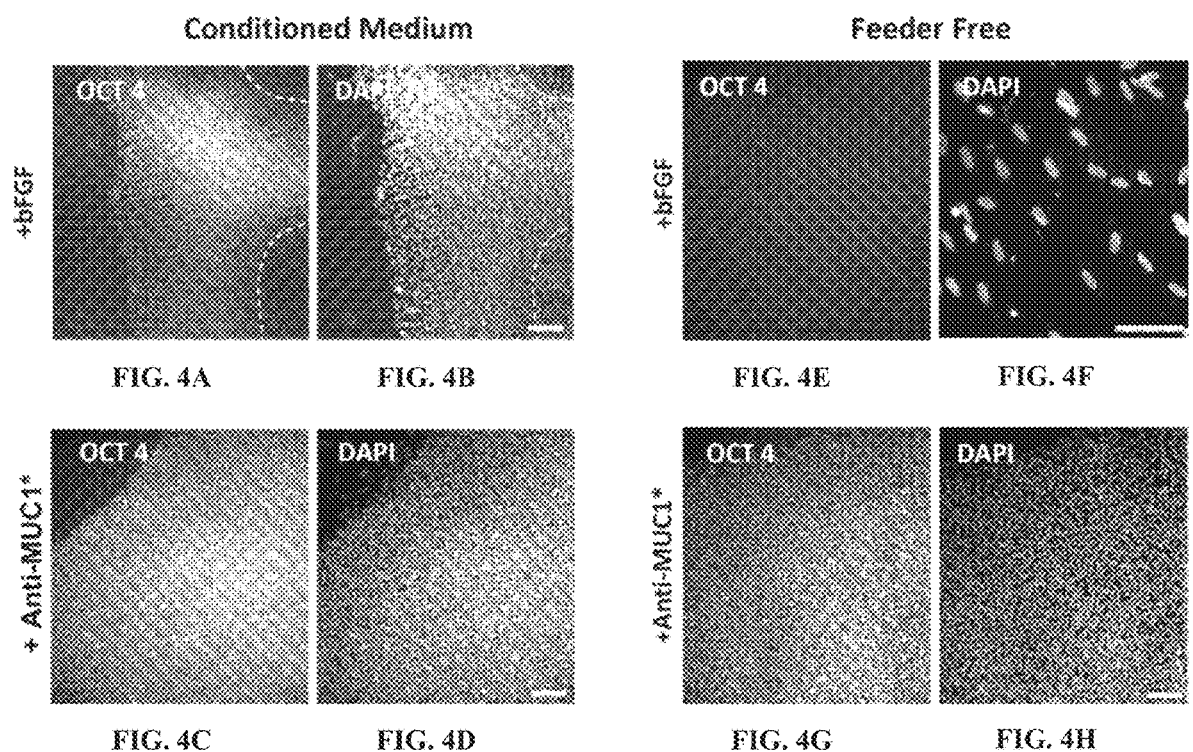

Long term growth of pluripotent (OCT4-positive) hESC is mediated by MUC1* stimulation. hESCs were trypsin-dissociated and seeded in 8-well chamber slides pre-coated with MATRIGEL at $4 \times 10^4$ cells/well. Media was changed and antibodies added every other day at a final concentration of 1 µg/ml for bivalent anti-MUC1* until discrete colonies were visible. Culture conditions include 'minimal stem cell medium' (hESC media without feeder-conditioned medium) and Hs27-conditioned medium, with and without bFGF supplementation. For each condition, cells were grown in quadruplicate. Cells were washed with PBS and fixed, and OCT4 immunostaining was conducted as described above. FIG. 4, panels A-D are photos of cells grown over MATRIGEL and conditioned medium from fibroblast feeder cells added. Panels E-H are photos of cells grown over MATRIGEL in which no conditioned medium from fibroblast feeder cells was added. The addition of anti-MUC1* antibody to cell cultures (FIG. 4 C, D) resulted in more pluripotent stem cells than growth supplemented by bFGF (FIG. 4A, B). The addition of anti-MUC1* antibody to cells cultured in the absence of conditioned medium from fibroblast feeder cells (FIG. 4 G, H) resulted in an abundance of pluripotent stem cells, in sharp contrast to cells grown by adding bFGF (FIG. 4 E, F), which resulted in no pluripotent cells (absence of OCT4).

Example 7

The effect of stimulating MUC1* to enhance the growth of pluripotent stem cells was directly measured in a quantitative Calcein assay. Human embryonic stem cells (hESCs) were manually dissected and grown on MATRIGEL-coated wells of a 96 well plate at a density of $1.9 \times 10^4$ cells/well. Culture media contained hESC media supplemented with 30% Hs27-conditioned medium and 4 ng/ml bFGF. Antibodies were added at a final concentration of 1 µg/ml for bivalent anti-MUC1* and 100 µg/ml for monovalent anti-MUC1*. Experiments were performed in triplicate. 41 hours-post antibody treatment, live and dead cells were quantified with the LIVE/DEAD viability/cytotoxicity kit (Molecular Probes), following manufacturer's instructions. Fluorescence was measured using a VICTOR3V plate reader (Perkin Elmer). The bar graph of FIG. 5 shows that stimulation of MUC1* using a dimerizing ligand (anti-MUC1*) enhanced stem cell growth, while blocking the extracellular domain of MUC1*, with the anti-MUC1* Fab, resulting in total stem cell death.

Example 8

A long-term stem cell growth experiment was done to compare the effects of stimulating the growth of stem cells using a bivalent anti-MUC1* antibody, NM23, NM23-mutant, or bFGF. hESCs were dissociated with trypsin and seeded in 8-well chamber slides pre-coated with MATRIGEL at a cell density of $8.2 \times 10^4$ cells/well. Media was changed and antibodies or wild type or mutant NM23 proteins were added every other day at final concentrations of 80 ng/ml for Anti-MUC1* antibody, 1 nM for wild type recombinant NM23 or mutant (S120G) NM23, or recombinant bFGF at a final concentration of 4 ng/ml in 'minimal stem cell medium' (hESC media without feeder-conditioned medium). Cells were also grown as a control in minimal stem cell medium with 30% conditioned medium from Hs27 fibroblasts and 4 ng/ml recombinant bFGF (Peprotech #100-18B). Results of this experiment show that MUC1* ligands do a better job of stimulating growth in minimal media of pluripotent colonies than does conditioned media plus bFGF, the 'normal' growth medium of these cells on MATRIGEL. Table 1 details the results.

TABLE 1

| | hESCs cultured in minimal media for 4 weeks | | |
|---|---|---|---|
| Growth condition | Week 1st colony appeared | Number of colonies | Morphology |
| Minimal Stem Cell Growth Media | | | |
| NM23 1 nM | Week 2 | 2 colonies | 2 large undifferentiated colonies in 1 of 1 wells; centers of colonies appear to begin to differentiate during week 3; by end of week 4, most of each colony remains undifferentiated |
| NM23-S120G mutant 1 nM | Week 2 | 7 colonies | 7 large undifferentiated colonies in 1 of 1 wells; centers of colonies appear to begin to differentiate during week 3; by end of week 4, most of each colony remains undifferentiated |
| anti-MUC1* 80 ng/ml | Week 2 | 5 colonies | 7 large undifferentiated colonies in 1 of 2 wells; centers of colonies appear to begin to differentiate during week 3; by end of week 4, most of each colony remains undifferentiated |
| bFGF 4 ng/ml | — | 0 | No colonies |
| nothing | Week 2 | 2 colonies | 2 very small, differentiated colonies |
| Control - 30% Conditioned Media from Hs27 Fibroblast Feeder Cells | | | |
| bFGF 4 ng/ml | Week 2 | 5 | 5 mostly differentiated colonies |

Example 9

Figure 6:
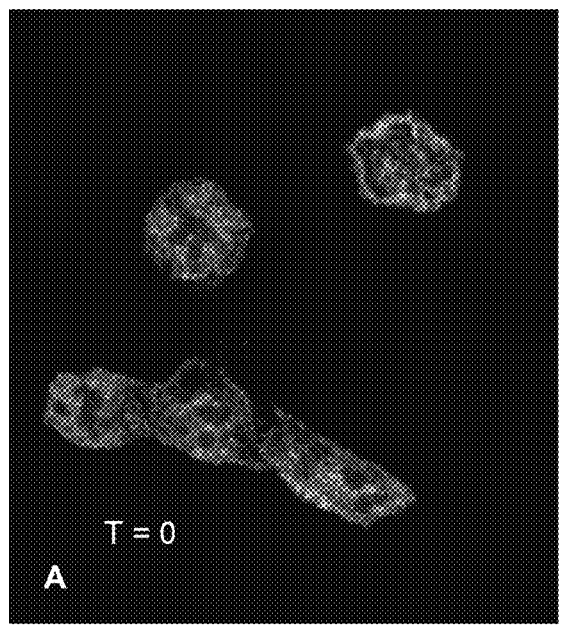
Figure 6:
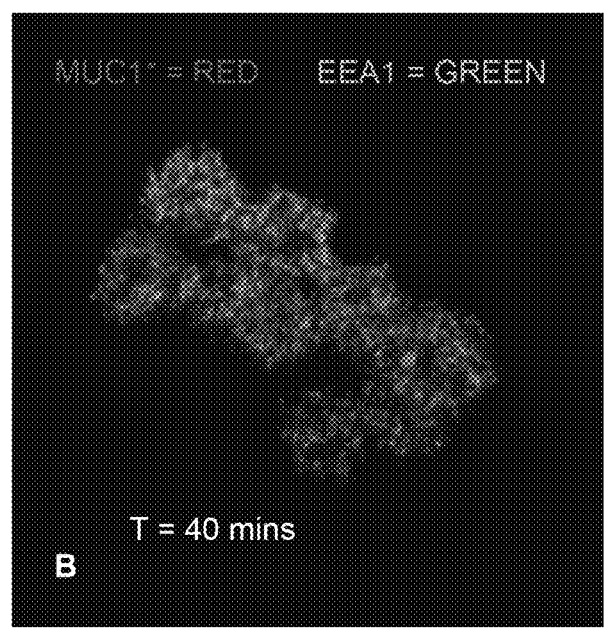

MUC1* translocates to nucleus of cells. Anti-MUC1* monoclonal Ab was labeled in vitro with ALEXA 555 dye, and bound at 4 C to HCT-116 cells (MUC1-negative) transfected with MUC1*, that had been washed in cold PBS, at 4 C. After 20 min, cells were washed twice in cold PBS, and cells were either fixed in 4% paraformaldehyde, or incubated with pre-warmed growth medium. Cells were washed after 40 minutes, and fixed with 4% paraformaldehyde for 5 minutes, then blocked and permeabilized with 2.5%, BSA 2.5% FBS and 0.1% NP-40 in PBS. Endosomes were stained using an anti-EEA1 antibody (Cell Signaling Technologies, 2411S) and ALEXA488 (Invitrogen 1:200) (FIG. 6).

Example 10. MUC1* Translocates to the Nucleus where it Functions as a Transcription Factor or Co-Factor It was previously reported in the scientific literature that an artificially expressed peptide, corresponding to the cytoplasmic domain of MUC1 (MUC1-CD), translocated to the nucleus (Huang, et al. 2005). Another study reported that the MUC1-CD bound to the p53 promoter site (Wei, et al. 2007). The Wei et al., 2007, report did not however determine whether in this capacity, the MUC1-CD up- or down-regulated transcription of p53. To induce or maintain stemness or pluripotency, it is desirable to suppress p53 (Maimets, et al., 2008). Further, the forced expression of the cytoplasmic domain of MUC1, alone, does not correspond to any naturally occurring state or cleavage state of MUC1. We therefore sought to determine whether or not it was actually MUC1*, which is a marker of pluripotency, that is translocated to the nucleus.

A polyclonal antibody, anti-MUC1*, that recognizes the PSMGFR epitope on MUC1* but not the same epitope when MUC1 is full-length (Mahanta et al 2008) was used to stain human embryonic stem cells according to the methods of Hikita et al (2008). Embryonic stem cells exclusively express MUC1* but not full-length MUC1. Immunocytochemistry showed that MUC1* was often detected in the nuclei of embryonic stem cells. A fluorescently tagged anti-MUC1* Fab fragment was incubated with cells that had been transfected with MUC1* or the empty vector. Excess Fab was removed, and cells were either washed at 4° C. in PBS and fixed in paraformaldehyde, or incubated with prewarmed medium at 37° C. for 10 min, 25 min, or 40 min to facilitate receptor internalization before paraformaldehyde fixation. Cells were moved to 4° C. to stop receptor internalization at various timepoints. The Fab bound specifically to MUC1*-transfected cells, and not to vector-transfected cells (data not shown). FIG. 6 shows that after 40 minutes, MUC1* is translocated to the nucleus of the cell.

Example 11. Inhibit p53 and its Pro-Apoptotic and Growth Inhibitory Effects, Using MUC1-Associated Factors, to Increase the Efficiency of Generating iPS (Induced Pluripotent Stem) Cells The small molecule Nutlin increases activity of p53 by interfering with the interaction between p53 and its natural inhibitor hDM2 (Vassilev et al., 2004). The induction of p53 activity by Nutlin drives the differentiation of human embryonic stem cells (Maimets, et al., 2008). Similarly, overexpression of p53 in embryonic stem cells inhibits hESC growth, most likely through the induction of apoptosis (Maimets, et al., 2008). In p53-null mice, the establishment of primary tumors was enhanced (Zhou et al., 2000). Thus, interfering with p53 activity increases the efficiency of establishing iPS cell lines.

During the establishment of novel iPS lines using a "core set" of pluripotency genes, OCT4, SOX2 and KLF4, induction of pluripotency is enhanced by inhibiting p53 first by the small molecule Nutlin and then by introducing MUC1*. MUC1* is introduced to cells undergoing induction of pluripotency by: 1) transfecting DNA that encodes MUC1*; and b) by adding a recombinant MUC1* protein that has been modified with a poly-arginine tract to efficiently enter the cell.

The core set of pluripotency genes was transfected into dermal fibroblasts. However, the exogenous expression of the direct or indirect gene products into dermal fibroblasts or other mature cells is also anticipated. The invention also anticipates that the addition of MUC1, MUC1* or associated factors can eliminate some, or all, of the core set of pluripotency factors.

Induction of pluripotency is also enhanced when a peptide corresponding to the cytoplasmic tail of MUC1 is exogenously added to cells undergoing conversion to pluripotency. Optionally, MUC1-CD is modified with a leader sequence such as a poly-Arginine tract that allows the peptide to enter the cell.

Example 12. The Introduction of MUC1-Related Proteins Enhances Pluripotency by Inducing Transcription of c-myc and by Activating MUC1* c-Myc has been shown to enhance the induction of pluripotency. NM23 induces transcription of c-myc (Dexheimer et al., 2009) and eliminates the need for c-myc. NM23 is introduced to cells undergoing conversion to iPS by transfection of the encoding nucleic acids or by exogenously adding the protein itself which may be modified with sequences, such as a poly-Arginine tract, to aid in cellular entry. NM23, wild type or mutant S120G that prefers dimer formation, is added to dermal fibroblasts that have been transfected with OCT4, SOX2 and KLF4. The efficiency of iPS cell generation is enhanced.

NM23 (NME-H1, NME-H2 or NME-7) enhances the induction or maintenance of pluripotency. NM23 is introduced along with previously identified pluripotency factors, including but not limited to OCT4, SOX2, KLF4, as well as others disclosed herein.

Example 13. Identification of a New Core Set of Pluripotency Factors that Include MUC1* Associated Factors MUC1* is introduced to cells to induce or maintain pluripotency or to improve the efficiency of iPSc formation or to replace one or more of the pluripotency gene set comprised of OCT4, SOX2, KLF4. A DNA construct containing nucleic acid encoding MUC1* is transfected into dermal fibroblasts along with combinations of the abovementioned set of pluripotency genes (or their gene products). The efficiency of iPS colony formation is determined by enumerating the number of stem cells generated. Further, cells are analyzed by immunofluorescent detection of pluripotency markers, such as OCT4, SSEA 1, 3, 4, TRA 1-60 TRA 1-81, TRA 2-49/6E (alkaline phosphatase), and NANOG. Resultant cells are evaluated for karyotype stability and the ability to differentiate along the three different germlines (mesoderm, endoderm and ectoderm). This is determined by immunofluorescent detection using antibodies against germline-specific markers, such as CD34 or smooth muscle actin for mesoderm detection, GATA-4 or cytokeratin 19 for endoderm detection, and Nestin or beta-III tubulin for ectoderm detection. A MUC1* activating ligand, preferably anti-MUC1* antibody or NM23 (NME), is optionally added to further enhance the induction or maintenance of pluripotency.

REFERENCES

Aoi, T. et al. Science 321, 699-702 (2008).
Boyer L. A. et al. Cell 122, 947-956 (2005)
Dexheimer at al. Mol Cancer Ther 8, 1363-1377 (2009)
Fessler S. et al. Breast Cancer Res Treat. May 5. (2009)
Foster, K. W. et al. Oncogene 24, 1491-1500 (2005)
Hikita et al. PLoS ONE 3, e3312 (2008)
Huang, L. et al. Cancer Res., 65(22):10413-22 (2005)
Huangfu D. et al. Nat Biotechnol 26, 795-797 (2008)(a)
Huangfu D. et al. Nat Biotechnol 26, 1269-1275 (2008)(b)
Jaenisch, R. and Young, R. Cell 132, 567-582 (2008)
Kaji K., et al. Nature 458:771-775 (2009)
Kawamura et al., Nature 460(7259), 1140-4 (2009)
Kim, et al. Biochem Biophys Res Commun 307: 281-289 (2003)
Komarov, et al. Science 285(5434), 1733-7 (1999)
Lin T et al. Nat Cell Biol 7, 165-171 (2005)
Lowry, W. E. et al. Proc. Natl. Acad. Sci. USA 105, 2883-2888 (2008).
Lyssiotis et al. Proc Natl Acad Sci USA 106, 8912-8917 (2009)
Mahanta et al. PLoS ONE 3, e2054 (2008)
Maherali, N. et al. Cell Stem Cell 1, 55-70 (2007).
Maimtes T et al., Oncogene 27, 5277-5287 (2008)
Nakagawa, M. et al. Nature Biotechnol 26, 101-106 (2008)
Okita, K et al. Nature 448, 313-317 (2007).
Okita K et al. Science 322, 949-953 (2009)
Park, I. H. et al. Nature 451, 141-146 (2008).
Raina et al. Cancer Res 69, 5133-5141 (2009)
Soldner F., et al. Cell 136:964-977 (2009)
Sommer C A et al., Stem Cells, 27(3), 543-9 (2009)
Stadtfeld M., et al. Science 322, 945-949 (2009)
Strom, et al. Nat Chem Biol. 2(9):474-9 (2006)
Takahashi, K. & Yamanaka, S. Cell 126, 663-676 (2006).
Takahashi, K. et al. Cell 131, 861-872 (2007).
Thathiah, A et al. J Biol Chem 274, 3386-3394 (2003)
Vassilev L. T. et al., Science 303, 844-848. (2004)
Wei et al. Cancer Res 67, 1853-1858 (2007)
Wernig, M. et al. Nature 448, 318-324 (2007).
Wernig M. et al. Cell Stem Cell 2, 10-12 (2008)
Woltjen K., et al. Nature 458, 766-770 (2009)
Yamanaka, S. Cell stem Cells 1, 39-49 (2007)
Yu J. et al. Science 324, 797-801 (2009)
Yu, J. et al. Science 318, 1917-1920 (2007)
Zhou et al. MCB, 20, 628-633 (2000
Zhou et al. Cell Stem Cell 4, 381-384 (2009)

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method for maintaining cell pluripotency or cell stemness, the method comprising:

contacting a cell characterized by an expression of OCT4 with an effective amount of an exogenous nucleoside diphosphate protein kinase 7 (NME7), thereby maintaining the expression of the OCT4 in the cell.

2. The method of claim 1, wherein the NME7 is a polypeptide.

3. The method of claim 1, wherein the cell is a stem cell.

4. The method of claim 1, wherein the cell is an undifferentiated embryonic stem cell (ESC) or a pluripotent stem cell.

5. The method of claim 1, wherein the cell is a human cell.

6. The method of claim 1, wherein said contacting comprises contacting a plurality of cells that comprises the cell.

7. The method of claim 1, wherein said contacting occurs in vitro.

8. The method of claim 1, wherein said contacting occurs in the absence of one or more feeder cells or an extract thereof.

9. The method of claim 1, wherein said contacting occurs in the absence of a basic fibroblast growth factor (bFGF).

10. The method of claim 1, wherein the method stimulates or enhances the growth of the cell.

11. A method for inducing pluripotency in a cell, the method comprising:

contacting the cell with transcription factors Oct4, Sox2, and Nanog, and contacting the cell with an exogenous nucleoside diphosphate protein kinase 7 (NME7).

12. The method of claim 11, wherein the NME7 is a polypeptide.

13. The method of claim 11, wherein the cell is a fibroblast.

14. The method of claim 11, wherein the cell is a human cell.

15. The method of claim 11, wherein the method produces an induced pluripotent cell.

16. The method of claim 11, wherein said contacting occurs in vitro.

17. The method of claim 11, further comprising contacting the cell with one or more transcription factors selected from Klf4, c-Myc, and Lin28.

18. The method of claim 11, wherein contacting the cell with transcription factors comprises introducing nucleic acids encoding said transcription factors into the cell.

* * * * *